US008627709B2

(12) United States Patent
Caron et al.

(10) Patent No.: US 8,627,709 B2
(45) Date of Patent: Jan. 14, 2014

(54) POROUS MEDIUM SENSOR

(75) Inventors: Jean Caron, Saint-Romuald (CA); Philippe Jobin, Saint-Gabriel-de-Valcartier (CA); Christian Plourde, Québec (CA); Jocelyn Boudreau, Lévis (CA); Sébastien Descôteaux, Saint-Jean-Chrysostome (CA); Daniel Belleau, Sainte-Hélène-de Breakeyville (CA)

(73) Assignee: Hortau Inc., St-Romuald, Quebec (CA)

( * ) Notice: Subject to any disclaimer, the term of this patent is extended or adjusted under 35 U.S.C. 154(b) by 725 days.

(21) Appl. No.: 12/770,945

(22) Filed: Apr. 30, 2010

(65) Prior Publication Data

US 2010/0263436 A1    Oct. 21, 2010

Related U.S. Application Data

(63) Continuation-in-part of application No. PCT/CA2008/001549, filed on Aug. 29, 2008.

(60) Provisional application No. 60/984,610, filed on Nov. 1, 2007.

(51) Int. Cl.
*G01N 7/10* (2006.01)
*G01N 33/24* (2006.01)

(52) U.S. Cl.
USPC .................................................. 73/38; 73/73

(58) Field of Classification Search
USPC ......................................................... 73/73, 38
See application file for complete search history.

(56) References Cited

U.S. PATENT DOCUMENTS

| 3,939,699 | A | * | 2/1976 | McCormick ...................... 73/73 |
| 5,046,282 | A | | 9/1991 | Whitaker |
| 5,179,347 | A | | 1/1993 | Hawkins |
| 5,851,491 | A | * | 12/1998 | Moulton ......................... 422/535 |
| 6,308,563 | B1 | | 10/2001 | Hubbell et al. |
| 6,539,780 | B2 | | 4/2003 | Hubbell et al. |
| 6,938,461 | B1 | | 9/2005 | Johnson |
| 2008/0041170 | A1 | * | 2/2008 | Jobin et al. ................ 73/862.581 |

FOREIGN PATENT DOCUMENTS

| EP | 1396722 | | 3/2004 |
| EP | 1921449 | * | 5/2008 |

OTHER PUBLICATIONS

Verdonck, O. F., Cappaert, T. M. and De Boodt, M. F. 1978. Physical characterization of horticultural substrates. Acta Hort. 82: 191-200. (artificial growing media).
Koorevaar, P., G. Menelik et C. Dirksen. Elements of soil physics, Elsevier, 1983, ISBN 0-444-42242 , Netherlands, p. 80-85. (mineral soils).

* cited by examiner

Primary Examiner — Daniel S Larkin
(74) Attorney, Agent, or Firm — Price Heneveld LLP

(57) ABSTRACT

A porous medium sensor apparatus includes a sensing portion at least partially insertable in the porous medium. The sensing portion has a housing with a gas exchange aperture defined therein and a water-repellant membrane mounted in the gas exchange aperture, the water-repellant membrane preventing water communication through the gas exchange aperture. The sensing portion also has a parameter sensor mounted in the housing for measuring a parameter of the porous medium in which the sensing portion is inserted.

21 Claims, 10 Drawing Sheets

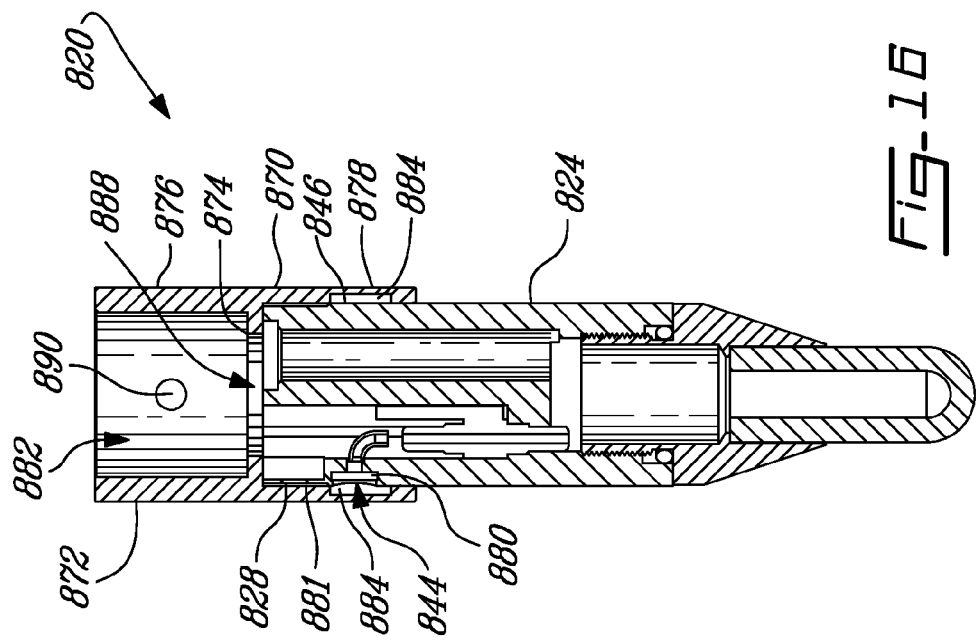
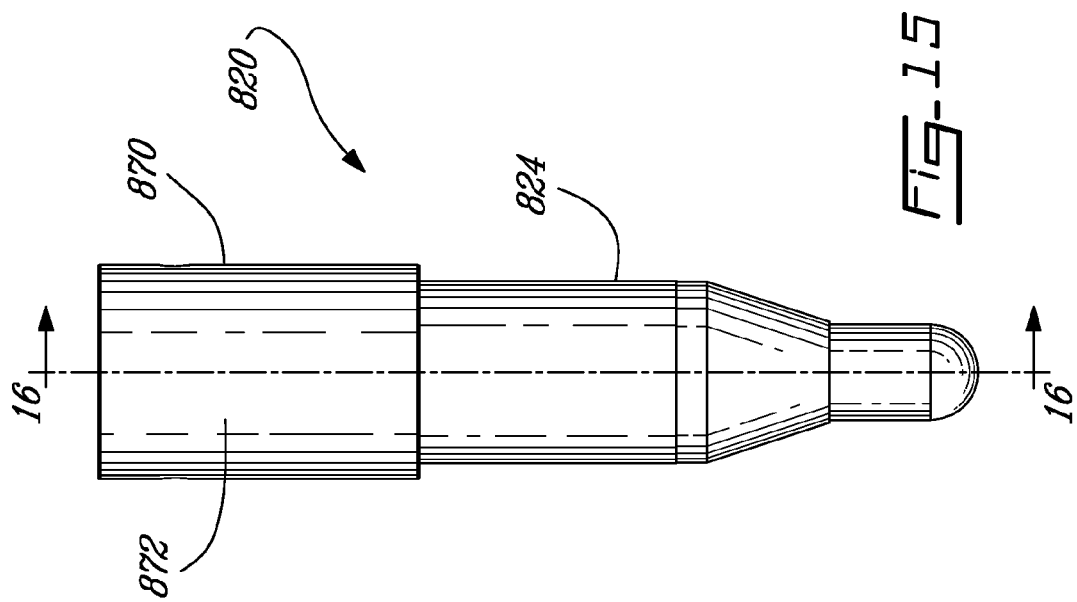

POROUS MEDIUM SENSOR

CROSS-REFERENCE TO RELATED APPLICATIONS

This application claims priority under 35 USC §119(e) of U.S. provisional patent application 60/984,610 filed on Nov. 1, 2007, the specification of which is hereby incorporated by reference. This application is a continuation-in-part of PCT patent application serial number PCT/CA2008/001549 filed Aug. 29, 2008, designating the United States of America, now pending, the specification of which is hereby incorporated by reference.

FIELD OF THE INVENTION

The invention relates to porous medium sensors for measuring parameters or properties in porous media and, more particularly, it relates to a porous medium sensor having a sensing portion entirely insertable in the porous medium.

DESCRIPTION OF THE PRIOR ART

Porous medium sensors for monitoring parameters in soil are known.

For example, tensiometers monitor matrix water potential $\Psi_m$ (or soil moisture tension). Matrix water potential is an indirect measure of soil water content. Tensiometers are used in irrigation scheduling to help farmers and other irrigation managers to determine when to water. In conjunction with a water retention curve, tensiometers can be used to determine how much to water. Tensiometers can also be used in the scientific study of soils and plants behavior.

Typically the sensors are partially inserted in growing media, such as soil, for monitoring purposes, i.e. they include a sensing portion which is inserted in the growing medium and a head which extends outwardly. A section of the housing can also extend outwardly of the growing medium.

For example, FIG. 1 shows a tensiometer 20 partially inserted in the growing medium for monitoring soil moisture tension, i.e. it has a porous tip 22 inserted in the growing medium, a housing 24 partially inserted in the growing medium, and a head 36 extending outwardly of the growing medium.

The tensiometer 20 includes a pressure sensor 26 having two ports, a first one 28 in fluid communication with the porous tip 22 and a second one 30 in gas communication with ambiant air, i.e. the reference port for tension measurement purposes. The second port 30 is in gas communication with an opening 32, defined in the housing 24, located outwardly of the growing medium when the tensiometer 20 is inserted therein. Accidental water and porous medium infiltrations in the housing 24 can occur through the opening 32, even if the latter is located above the growing medium. Water and porous medium infiltrations can bias the matrix water potential measures when obstructing the opening 32. Moreover, in some application, it might be desirable to have a tensiometer that is entirely insertable in the growing medium.

BRIEF SUMMARY OF THE INVENTION

It is therefore an aim of the present invention to address the above mentioned issues.

According to an aspect, there is provided a porous medium sensor apparatus comprising: a sensing portion at least partially insertable in the porous medium, the sensing portion having a housing with a gas exchange aperture defined therein and a water-repellant membrane mounted to the gas exchange aperture, the water-repellant membrane preventing water communication through the gas exchange aperture; and a parameter sensor mounted in the housing for measuring a parameter of the porous medium in which the sensing portion is inserted.

In an embodiment, the sensing portion comprises an internal chamber in gas communication with at least one of the porous medium in which the sensing portion is at least partially inserted, and the atmosphere through the water-repellant membrane. The sensing portion can comprise a porous tip mounted to the housing, insertable in the porous medium simultaneously with the sensing portion, having pores fillable with liquid solution characteristic of the porous medium in which the sensing portion is at least partially inserted. The water-repellant membrane can be in direct gas communication with a port of the parameter sensor. The water-repellant membrane can be porous and gas permeable.

In an embodiment, the water-repellant membrane has a first face contacting at least one of the porous medium when the sensing portion is at least partially inserted therein and atmospheric gas and a second face, opposed to the first face and extending in the housing, gas pressures on the first and the second faces of the water-repellant membrane being substantially equal.

The water-repellant membrane can comprise a material selected from the group comprising: porous hydrophobic polypropylene and porous hydrophobic polyethylene.

In an embodiment, the sensing portion comprises a matrix water potential sensing portion and the parameter sensor comprises a pressure sensor having a first port in fluid communication with the porous medium and providing an indication of liquid pressure in the porous medium and a second port in gas communication with the water-repellant membrane and providing an indication of atmospheric gas pressure.

The second port and the water-repellant membrane can be in gas communication through a gas channel extending in the housing.

The parameter sensor can be selected from the group comprising: an electrical transducer, a pressure sensor, a H+-selective transducer, an ion-selective transducer, a temperature sensor, a humidity sensor, a liquid sensor, and a gas sensor. The sensing portion can be selected from the group comprising: a salinity sensor, an ion-selective sensor, a pH sensor, a tensiometer, a gas sensor, a gas concentration sensor, a humidity sensor, a liquid sensor, and a temperature sensor.

In an embodiment, the water-repellant membrane is a hydrophobic membrane.

In an embodiment, the porous medium sensor apparatus comprises a tube connectable to the gas exchange aperture, orientable to extend above the housing, and allowing gas exchange between atmosphere and the gas exchange aperture.

According to another aspect, there is provided a porous medium sensor apparatus for measuring a parameter in a porous medium, the porous medium sensor apparatus comprising: a housing at least partially insertable in the porous medium and having at least one gas exchange aperture and a membrane inserted in the at least one gas exchange aperture, the membrane preventing water infiltration in the housing through the at least one gas exchange aperture and allowing gas communication between atmosphere and the housing; a porous tip mounted to the housing, insertable in the porous medium simultaneously with the housing, having pores fillable with liquid solution, and the pores being in gas communication with the housing through a one-way flow control member, gas communication between the porous tip and atmosphere being allowed via the one-way flow control member and the membrane; and a sensor mounted in the housing and measuring a quantity in said liquid solution, the pores of the porous tip being in fluid communication with the sensor, said quantity being representative of said parameter in said porous medium.

In an embodiment, the housing comprises an internal chamber, the membrane preventing water infiltration in the internal chamber through the at least one gas exchange aperture and allowing gas communication between atmosphere and the internal chamber, the pores of the porous tip being in gas communication with the internal chamber through the one-way flow control member.

In an embodiment, the housing comprises a gas exchange channel having a first port connected to the one-way flow control member and a second port connected to the membrane, the membrane preventing water infiltration in the gas exchange channel through the at least one gas exchange aperture and allowing gas communication between atmosphere and the gas exchange channel, the pores of the porous tip being in gas communication with the gas exchange channel through the one-way flow control member.

The membrane can be in gas communication with a port of the sensor. The membrane can be a hydrophobic membrane and/or porous and gas permeable.

In an embodiment, the membrane has a first face contacting at least one of atmosphere and the porous medium when the housing is at least partially inserted therein and a second face, opposed to the first face and extending in the housing, gas pressures on the first and the second faces of the membrane being substantially equal.

In an embodiment, the membrane comprises a material selected from the group comprising: porous hydrophobic polypropylene and porous hydrophobic polyethylene.

In an embodiment, the sensor comprises a pressure sensor having a first port in fluid communication with the porous medium through the porous tip and providing an indication of liquid pressure in the porous medium and a second port in gas communication with the membrane and providing an indication of atmospheric gas pressure.

The second port and the membrane can be in gas communication through a gas exchange channel extending in the housing. Furthermore, the second port and the membrane can be in gas communication through a liquid free chamber defined in the housing.

The sensor can be selected from the group comprising: an electrical transducer, a pressure sensor, a H+-selective transducer, an ion-selective transducer, a temperature sensor, a liquid sensor, a humidity sensor, and a gas sensor. The porous medium sensor apparatus can be selected from the group comprising: a salinity sensor, an ion-selective sensor, a pH sensor, a tensiometer, a gas sensor, a gas concentration sensor, a liquid sensor, a humidity sensor, and a temperature sensor.

According to a still another aspect, there is provided a porous medium sensor apparatus for measuring a parameter in a porous medium, the porous medium sensor apparatus comprising: a housing at least partially insertable in the porous medium and having a gas aperture with a hydrophobic membrane covering the gas aperture, the hydrophobic membrane preventing water infiltration in the housing therethrough and allowing gas communication with atmosphere; and a parameter sensor mounted in the housing and having a reference port in gas communication with the membrane.

In an embodiment, the porous medium sensor further comprises a porous tip mounted to the housing, insertable in the porous medium simultaneously with the housing, having pores fillable with liquid, and the pores being in fluid communication with the parameter sensor, the parameter sensor providing an indication of the parameter in the porous medium.

The hydrophobic membrane can be insertable in the porous medium when the housing is inserted therein and it can be porous and gas permeable.

In an embodiment, the hydrophobic membrane has a first face contacting at least one of the atmosphere and the porous medium when the housing is at least partially inserted therein and a second face, opposed to the first face and extending in the housing, gas pressures on the first and the second faces of the hydrophobic membrane being substantially equal.

In an embodiment, the housing comprises an internal chamber in gas communication with at least one of the atmosphere and the porous medium in which the housing is at least partially inserted through the hydrophobic membrane.

The hydrophobic membrane can comprise a material selected from the group comprising: porous hydrophobic polypropylene and porous hydrophobic polyethylene.

In an embodiment, the parameter sensor comprises a pressure sensor having a first port in fluid communication with the porous medium and providing an indication of liquid pressure in the porous medium and a second port in gas communication with the hydrophobic membrane and providing an indication of atmospheric gas pressure. The second port and the hydrophobic membrane can be in fluid communication through a gas channel extending in the housing. The second port and the hydrophobic membrane can be in gas communication through a liquid free chamber defined in the housing.

The parameter sensor can be selected from the group comprising: an electrical transducer, a pressure sensor, a H+-selective transducer, an ion-selective transducer, a temperature sensor, a liquid sensor, a humidity sensor, and a gas sensor.

According to a further aspect, there is provided a matrix water potential sensor comprising: a sensing portion at least partially insertable in a porous medium and having a housing with a gas aperture defined therein and a water-repellant membrane extending over the gas aperture and preventing water infiltration in the housing; and a pressure sensor mounted in the housing and having a reference port in gas communication with atmosphere through the water-repellant membrane, a liquid port in fluid communication with the porous medium when the housing is inserted therein, the pressure sensor providing an indication of the matrix water potential by comparing liquid pressure in the liquid port and gas pressure in the reference port.

In an embodiment, the sensing portion comprises an internal chamber in at least one of gas communication with the porous medium in which the sensing portion is at least partially inserted through the water-repellant membrane and in liquid communication with the porous medium in which the sensing portion is at least partially inserted through the porous tip.

In an embodiment, the sensing portion comprises a porous tip mounted to the housing, insertable in the porous medium simultaneously with the housing, having pores fillable with liquid solution characteristic of the porous medium in which the sensing portion is inserted. The liquid port of the pressure sensor can be in liquid communication with the porous medium through the porous tip. The reference port and the water-repellant membrane can be in gas communication through a gas channel extending in the housing. The reference port and the water-repellant membrane can be in gas communication through an internal chamber defined in the housing.

The water-repellant membrane can be porous and gas permeable.

In an embodiment, the water-repellant membrane has a first face contacting at least one of atmosphere and the porous medium when the sensing portion is at least partially inserted therein and a second face, opposed to the first face and extending in the housing, gas pressures on the first and the second faces of the water-repellant membrane being substantially equal.

The water-repellant membrane can comprise a material selected from the group comprising: porous hydrophobic polypropylene and porous hydrophobic polyethylene.

According to another aspect, there is provided a porous medium tensiometer for measuring matrix water potential in a porous medium, the porous medium tensiometer comprising: a housing at least partially insertable in the porous medium and having a gas aperture with a membrane inserted therein, the membrane preventing water infiltration in the housing therethrough and allowing gas communication with atmosphere; a pressure sensor mounted in the housing and having a reference port in gas communication with the membrane; and a porous tip mounted to the housing, insertable in the porous medium simultaneously with the housing, having pores fillable with liquid, and the pores being in fluid communication with the pressure sensor, the pressure sensor providing an indication of the matrix water potential by comparing the pressures in atmosphere through the reference port and in the porous tip. The membrane can be inserted in the porous medium when the housing is inserted therein. The membrane can be porous and gas permeable and/or it can be a hydrophobic membrane.

In an embodiment, the pressure sensor has a liquid port in liquid communication with the porous tip.

In an embodiment, the membrane has a first face contacting at least one of atmosphere and the porous medium when the housing is at least partially inserted therein and a second face, opposed to the first face and extending in the housing, gas pressures on the first and the second faces of the hydrophobic membrane being substantially equal.

In an embodiment, the housing comprises an internal chamber, the membrane preventing water infiltration in the internal chamber through the at least one gas aperture and allowing gas communication between atmosphere and the internal chamber, the pores of the porous tip being in gas communication with the internal chamber through a one-way flow control member.

In an embodiment, the housing comprises a gas exchange channel having a first port connected to the reference port of the pressure sensor and a second port connected to the membrane, the membrane preventing water infiltration in the gas exchange channel through the at least one gas exchange aperture and allowing gas communication between atmosphere and the gas exchange channel.

The membrane can comprise a material selected from the group comprising: porous hydrophobic polypropylene and porous hydrophobic polyethylene.

According to a further aspect, there is provided a porous medium sensor apparatus comprising: a sensing portion at least partially insertable in the porous medium, the sensing portion having a housing with a gas exchange aperture defined therein and a cover mounted to the housing and covering the gas exchange aperture, the cover substantially preventing granular material to obstruct the gas exchange aperture while allowing gas communication between atmosphere and the gas exchange aperture; and a parameter sensor mounted in the housing for measuring a parameter of the porous medium in which the sensing portion is inserted.

In an embodiment, gas communication between atmosphere and the gas exchange aperture occurs through the porous medium wherein the porous medium sensor apparatus is at least partially inserted.

In an embodiment, the cover comprises a peripheral wall abutting the housing with a tightness substantially preventing granular material to infiltrate in between while allowing gas communication and having a recess defined internally therein in register with the gas exchange aperture.

In this specification, the term "porous medium" is intended to mean the soil of a field in agriculture, or the soil of pots for growing plants in a greenhouse or in a nursery, and any porous medium which fills with liquid. It can also be called a substrate, a mixture, a medium, or a soilless medium.

BRIEF DESCRIPTION OF THE DRAWINGS

FIG. 15 is a side elevation view of a tensiometer apparatus in accordance with another embodiment wherein the tensiometer apparatus includes a cover; and FIG. 16 is a sectional view taken along cross-section lines 16-16 of FIG. 15 of the tensiometer apparatus shown in FIG. 15.

It will be noted that throughout the appended drawings, like features are identified by like reference numerals.

DETAILED DESCRIPTION

Figure 2:
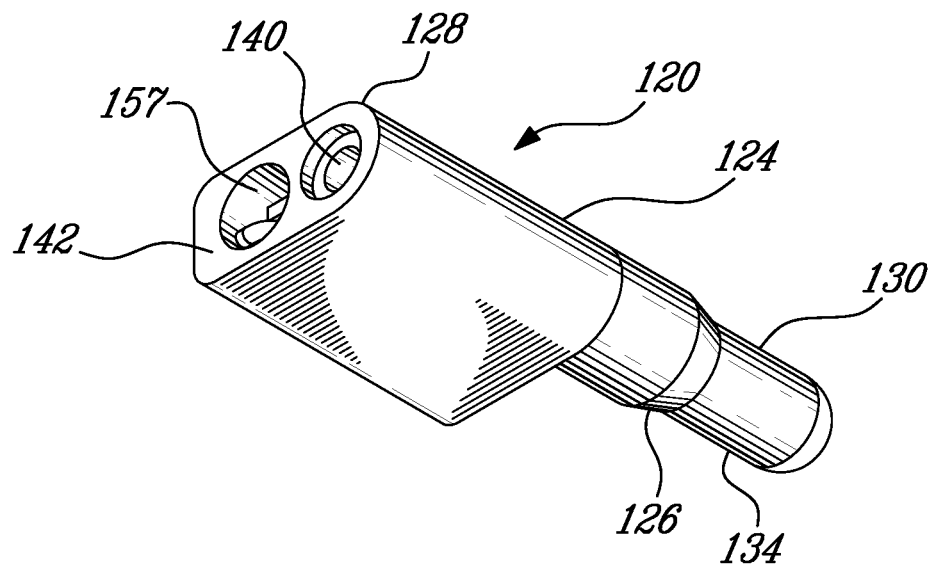
FIG. 2 is a perspective view of a tensiometer apparatus in accordance with a first embodiment.
Figure 3:
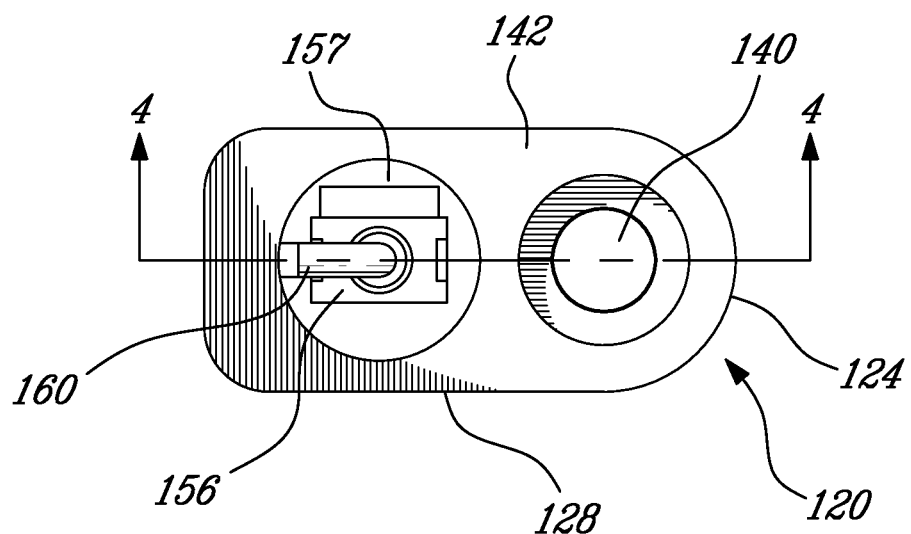
FIG. 3 is a top plan view of the tensiometer apparatus shown in FIG. 2.
Figure 4:
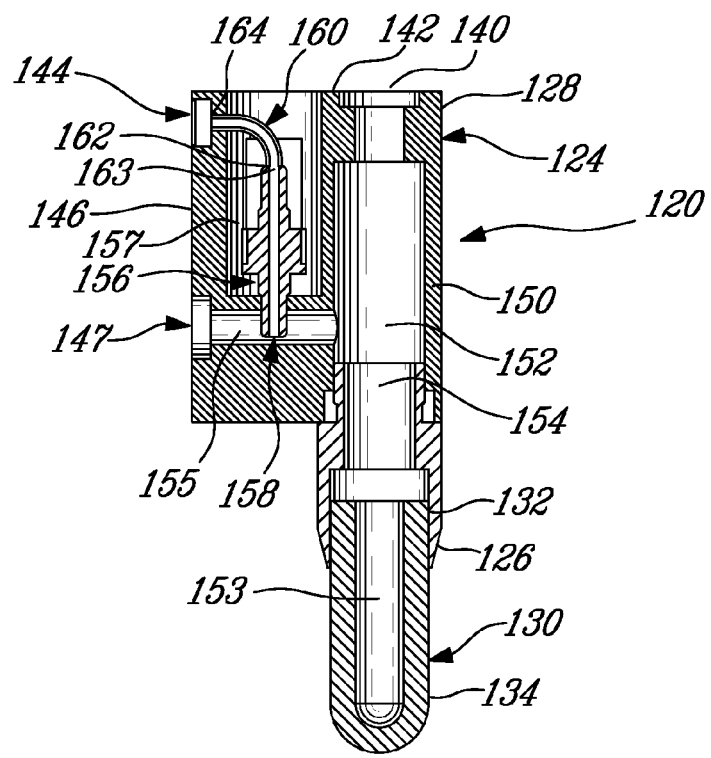
FIG. 4 is a sectional view taken along cross-section lines 4-4 of FIG. 3 of the tensiometer apparatus shown in FIG. 2.

Referring to the drawings and, more particularly, to FIGS. 2-4, it will be seen a sensing portion 120 of a porous medium sensor and, more particularly, a tensiometer apparatus (or water potential sensor) in accordance with an embodiment. The tensiometer is designed to monitor matrix water potential in a porous medium such as, for instance, earthen soil or greenhouse soil.

The sensing portion 120 has a housing 124 with a lower end 126 and an opposed upper end 128 and a porous material tip 130. The porous material tip 130 is mounted to the lower end 126 of the housing 124. The porous material tip 130 has a first section 132 which extends in the housing 124 and a second section 134 which is in direct contact with the porous medium when inserted therein, as will be described in more details below.

The sensing portion 120 can be connected to a head 336, which can include an antenna 338, as it will be described below in reference to FIG. 9. The head 336 and the antenna 338 can extend above the porous medium when the sensing portion 120 is at least partially inserted therein.

The housing 124 has a liquid inlet aperture 140 (or fluid aperture), located on an upper wall 142 of the housing 124, a gas inlet aperture 144, located on lateral wall 146 of the housing 124, and a machining aperture 147, also located on a lateral wall 146 of the housing 124. All apertures 140, 144, 147 extend throughout a respective wall of the housing 124. In an alternative embodiment, these apertures 140, 144, 147 can be positioned differently on the housing 124 or the housing 124 can include none, one or more of these apertures. The housing 124, including the liquid inlet aperture 140 and the gas inlet aperture 144, can be entirely insertable in the porous medium for monitoring matrix water potential, as described in more details below. It is appreciated that the design, the shape, and the components can vary.

Referring to FIG. 4, an embodiment of the internal structure of the sensing portion 120 will be described in more detail. The housing 124 has a peripheral wall 150 which defines a fluid chamber 152 therein. The fluid chamber 152 is substantially T-shaped with a first section 154, extending longitudinally in the housing 124, and a second section 155, extending transversally in the housing 124. Both sections 154, 155 are in fluid communication. The liquid inlet aperture 140 is located at a first end of the first section 154, opposite to the porous material tip 130. The machining aperture 147 is located at a first end of the second section 155, opposite to the junction of the first and second sections 154, 155.

The fluid chamber 152 is in fluid communication with the porous material tip 130 and, more particularly, with a central cavity 153 defined in the porous material tip 130 which is also fillable with liquid.

A pressure sensor 156, such as a pressure transducer, is located in the housing 124, in a pressure sensor chamber 157. The pressure sensor 156 is located above the second section 155 of the chamber 152, above the porous tip 130 without being inserted therein. The pressure sensor 156 has a liquid port 158 in fluid communication with the fluid chamber 152 and, more particularly, the second section 155. The fluid chamber 152 is designed to be filled with liquid, typically water, the pressure in the liquid being representative of the matrix water potential sampled through the porous material tip 130 when inserted in the porous medium.

The liquid pressure in the fluid chamber 152, sampled through the liquid port 158, is compared by the pressure sensor 156 to the atmospheric pressure. Therefore, the pressure sensor 156 is in gas communication with the atmosphere through an atmospheric gas channel 160 which extends in the housing 124. The atmospheric gas channel 160 has a first port 162 connected to a reference port 163 of the pressure sensor 156 and a second port 164 connected to the gas inlet aperture 144.

To prevent liquid and porous medium infiltration in the gas inlet aperture 144 and the atmospheric gas channel 160, a hydrophobic membrane 180 (FIG. 5), or water-repellent membrane, is inserted in the gas inlet aperture 144. The hydrophobic membrane 180 prevents partial or complete obstruction of the gas inlet aperture 144 and the atmospheric gas channel 160 which could bias the pressure measurements.

The hydrophobic membrane 180 is porous, gas permeable, i.e. it allows gas communication between the porous medium where the sensing portion 120 is inserted (or atmosphere) and the atmospheric gas channel 160. The pressure on both sides of the membrane 180, i.e. inwardly and outwardly of the housing 124 is substantially equal. The response time of the membrane 180 to reach equilibrium is substantially fast. In an embodiment, the membrane 180 can substantially resist to microbiologic and chemical degradation in porous media. The membrane shape, thickness, and size can vary in accordance with the tensiometer design or the design of any other porous medium sensor, as it will be described in more details below.

Figure 5:
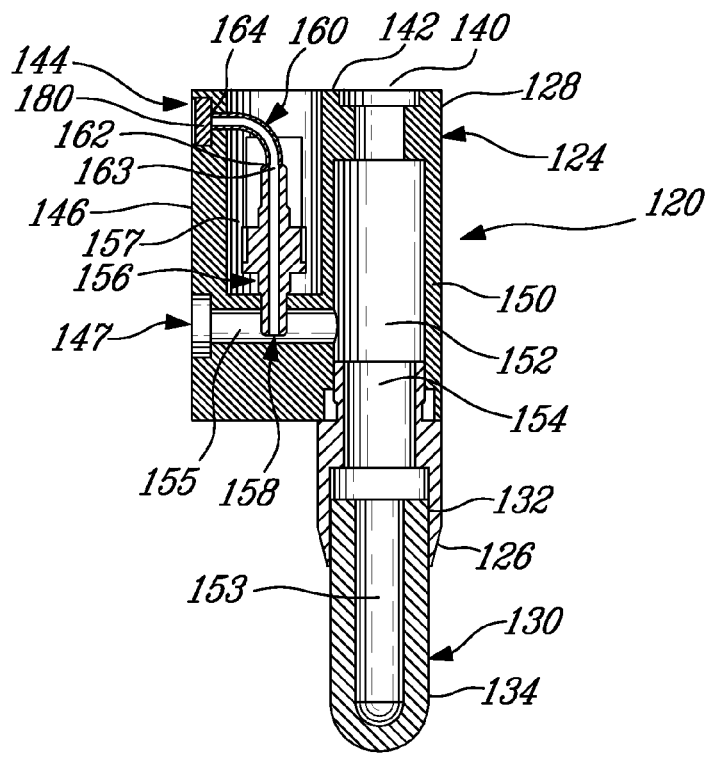
FIG. 5 is a sectional view taken along cross-section lines 4-4 of FIG. 3 of the tensiometer apparatus shown in FIG. 2, having a hydrophobic membrane inserted in a gas inlet aperture.

In an embodiment, the membrane 180 is shaped to fill the gas inlet aperture 144 defined in the housing 124 and is tightly inserted therein, as shown in FIG. 5. If an adhesive is used to secure the membrane 180 to the housing 124, care should be taken to prevent or minimize membrane pore obstruction with the adhesive.

If the porous medium includes components, such as chemical components, that could affect the membrane properties and obstruct the pores, the membrane material can be selected to repel also these components.

For instance, without being imitative to hydrophobic polypropylene and polyethylene porous sheets, manufactured with free-sintered materials, such as resins, can be used. These porous sheets provide filter media for ultra fine particles and flowability of gases. The filtration obtained varies depending on the micron size material selected.

The tensiometer can further include an electric wire channel (not shown) extending longitudinally in the housing 124. It has a first end connected to the pressure sensor 156, or indirectly to an electronic circuit mounted to the pressure sensor, and a second end connected to an electric circuit board (not shown) of the tensiometer apparatus. The electric wire channel contains electric wires (not shown) in which data acquired or monitored by the pressure sensor 156 are transferred to the electronic circuit board. The electric wire channel can also include electric wires which provide power supply to the pressure sensor and an electric circuit board operatively connected to the pressure sensor.

A fluid injector can be inserted in the liquid inlet aperture 140 for injecting a fluid therein and into the fluid chamber 152 for filling the latter. When inserted in the liquid inlet aperture 140, the fluid injector cannot wholly obstruct the liquid inlet aperture 140 thereby allowing simultaneously gas, previously contained in the fluid chamber 152, to exit therethrough while filling the fluid chamber 152 with liquid. When the fluid chamber 152 is filled with liquid, the liquid inlet aperture 140 is sealed and closed to prevent liquid contained in the fluid chamber 152 and in the porous material tip 130 to exit therethrough and prevents gas infiltration. In an embodiment, a seal and a cap (not shown) are inserted in the aperture 140 and secured therein. The seal can be an O-ring and the cap can be a pneumatic screw. In an embodiment, the seal and the cap are removable thereby allowing one to refill the fluid chamber 152, if necessary.

Before inserting the sensing portion 120 in the porous medium, the machining aperture 147, if any, is also sealed and closed to prevent liquid contained in the fluid chamber 152 to exit therethrough. In an embodiment, as with the liquid inlet aperture 140, a seal and a cap assembly (not shown), such as an O-ring and a pneumatic screw, can be inserted in the aperture 147 and secured therein.

The pressure sensor chamber 157 can be closed with a resin, such as epoxy, before inserting the sensing portion 120 in the porous medium. The resin prevents fluid and porous material infiltration in the pressure sensor chamber 157 and seals chamber 157.

To measure matrix water potential in a porous medium, the sensing portion 120, having a fluid chamber 152 substantially filled with liquid to ensure that the pressure sensor 156 is immerged, is first inserted in the porous medium.

Once the sensing portion 120 is connected to a power supply (not shown), if needed, the pressure sensor 156, monitors the matrix water potential in the porous medium where the sensing portion 120 is inserted. In accordance with the matrix water potential, liquid is either drawn into or rejected from the porous tip 130 and the pressure in the pores of the porous tip 130 varies accordingly. The pressure in the fluid chamber 152, which is in fluid communication with the porous material tip 130, also varies substantially simultaneously and accordingly. Therefore, the pressure sensor 156 compares the pressure of liquid contained in the fluid chamber 152 to atmospheric pressure, i.e. the sensor 156 measures the pressure caused by the water within the fluid chamber 152 as a function of atmospheric pressure. As mentioned above, atmospheric pressure is obtained through the atmospheric gas channel 160 which is in gas communication with the membrane 180. Liquid and porous material infiltration is prevented by the hydrophobic membrane 180 inserted in the aperture 144, even if the aperture 144 is located in the porous medium.

If the sensing portion 120 is entirely inserted in the porous medium, the atmospheric pressure is obtained through gas communication between atmosphere and the membrane 180 through the porous medium (or soil). Therefore, for pressure measurement purposes, it is assumed that gas pressure within the porous medium, at the sensing portion insertion depth, is substantially similar to atmospheric pressure. If the sensing portion is deeply inserted in the porous medium, an appropriate correction can be made to the measured pressure. The correction can be made either by the pressure sensor, by a second reference pressure sensor measuring pressure in the air, by the electronic circuit board, or any other component.

The data monitored are transferred to an electronic circuit board which can display, transmit and/or record the data.

In an alternative embodiment, the housing 124 can include an outwardly extending section (not shown), which can either be flexible or rigid. The outwardly extending section includes a gas channel having a first port in fluid communication with the reference port 163 of the pressure sensor 156 and a second port in which the hydrophobic membrane 180 is mounted and providing gas communication with atmosphere. If the sensing portion 120 is inserted deeply in the ground, the outwardly extending section of the housing can extend upwardly relatively to the porous tip 130. Therefore, no mathematical correction can be required for atmospheric gas pressure provided via the hydrophobic membrane 180.

If the sensing portion 120 is only partially inserted in the porous medium, the membrane 180 can extend outwardly of the porous medium and the membrane 180 can be in direct gas communication with atmosphere. In this alternative embodiment, the membrane 180 only prevents accidental liquid and porous medium infiltration in the housing 124.

Figure 1:
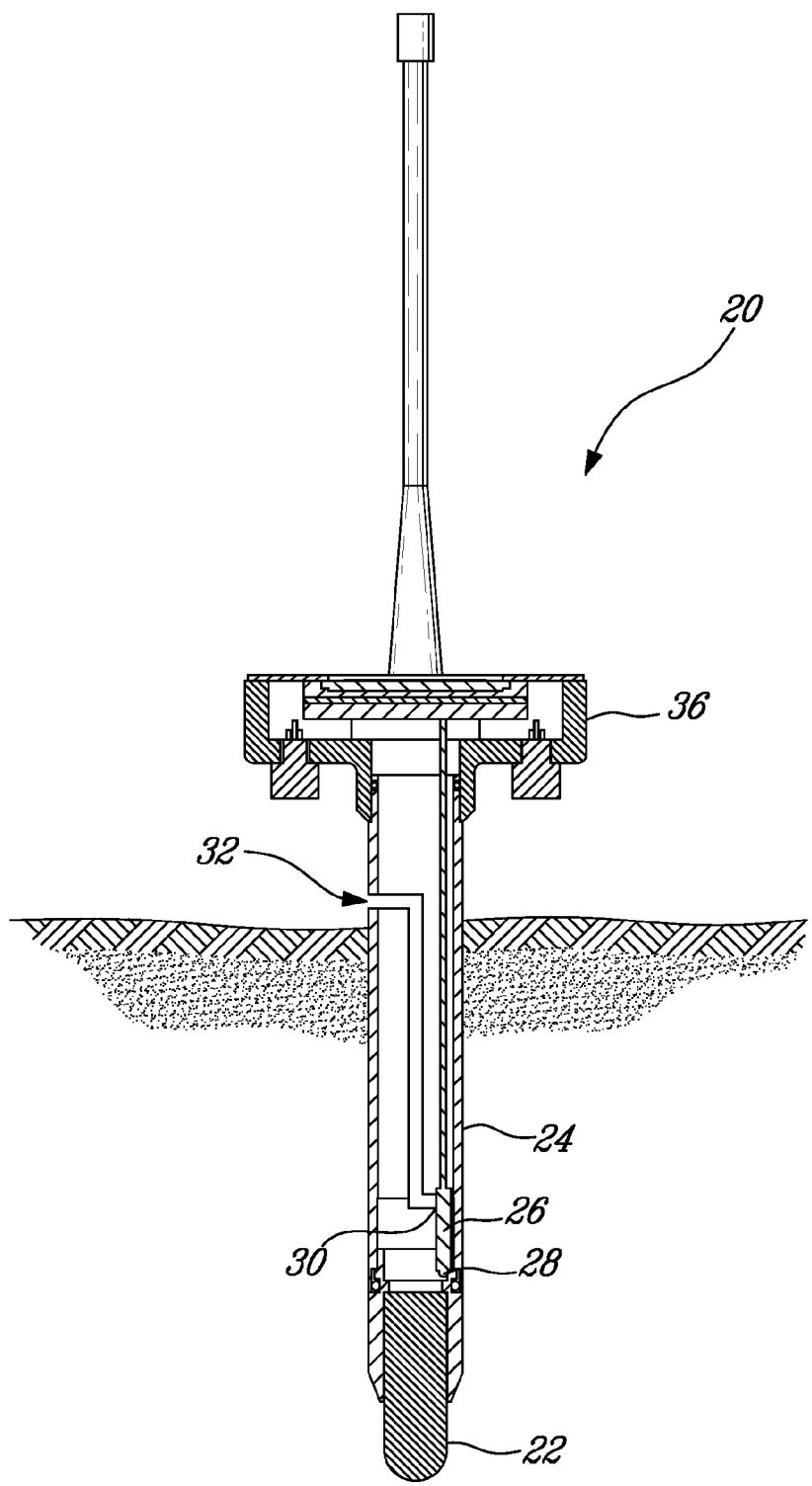
FIG. 1 is a cross-sectional view of a tensiometer apparatus, partially inserted in a growing medium, in accordance with an embodiment of the prior art.

Therefore, in that embodiment, the hydrophobic membrane 180 can be mounted to the atmospheric opening 32 of the conventional tensiometer shown in FIG. 1, i.e. tensiometers which are not entirely inserted in the porous medium. In that embodiment, the hydrophobic membrane 180 prevents accidental liquid and porous medium infiltration into the atmospheric opening 32.

In the embodiment shown, the hydrophobic membrane 180 is used with tensiometers having the pressure sensor 156 located externally of the fluid chamber 152.

It is appreciated that, in an alternative embodiment, the hydrophobic membrane 180 can be used with tensiometers having the pressure sensor 156 located in the fluid chamber 152. The pressure measurement side of the sensor 156 is open to the water contained with the fluid chamber 152 while the other end of the sensor 156, i.e. the reference port 163, is vented to the atmosphere through the hydrophobic membrane 180. An absolute pressure sensor may also be substituted for the sensor described above.

It is advantageous to position the sensor 156 proximate to the porous tip 130 since the sensor 156 is kept below the liquid level in the fluid chamber 152 and in fluid contact with both the liquid and the ambient atmosphere. The tensiometer therefore does not require pressure measurement corrections since liquid level variations within the fluid chamber 152 do not affect the monitored pressure measurement. The tensiometer monitors pressure changes relative to atmospheric pressure and is independent of changes in liquid level within the sensing portion 120.

Figure 6:
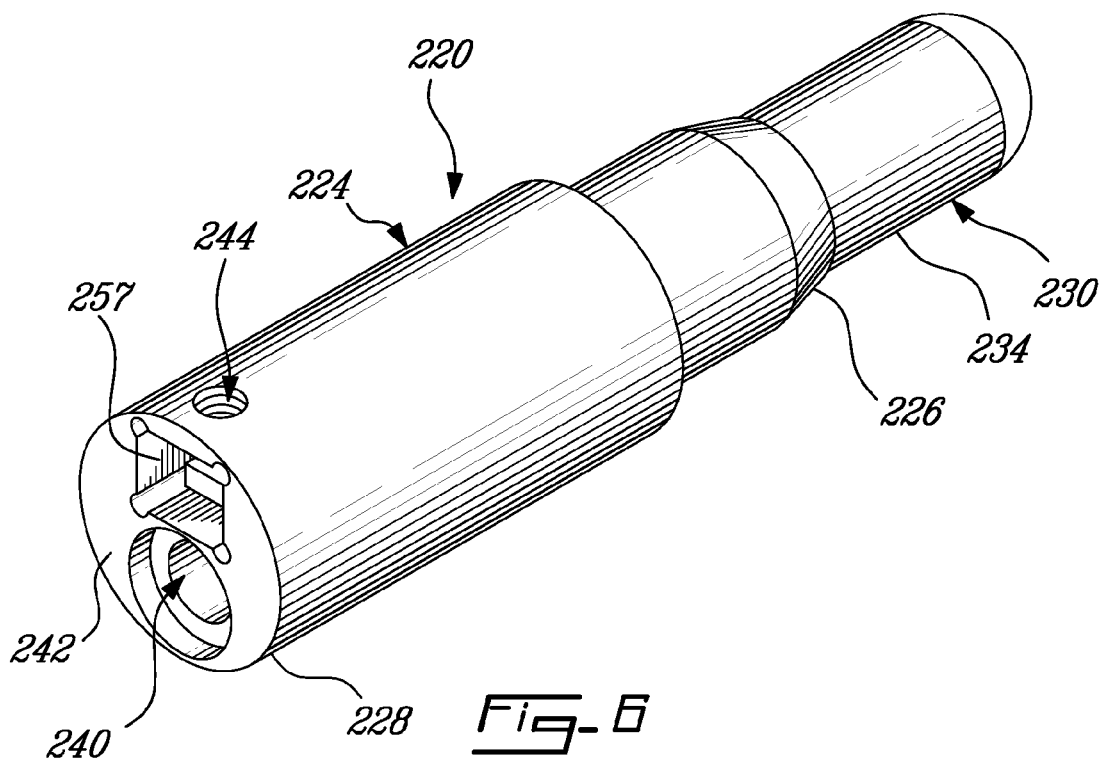
FIG. 6 is a perspective view of a tensiometer apparatus in accordance with a second embodiment, wherein the housing is substantially cylindrically shaped.
Figure 7:
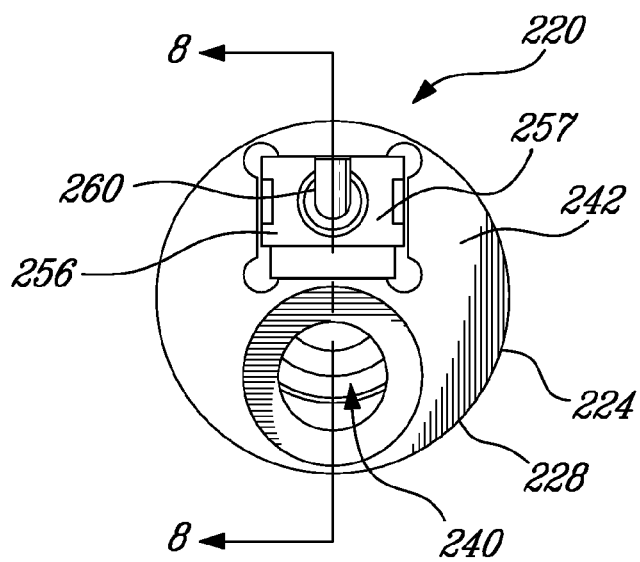
FIG. 7 is a top plan view of the tensiometer apparatus shown in FIG. 6.
Figure 8:
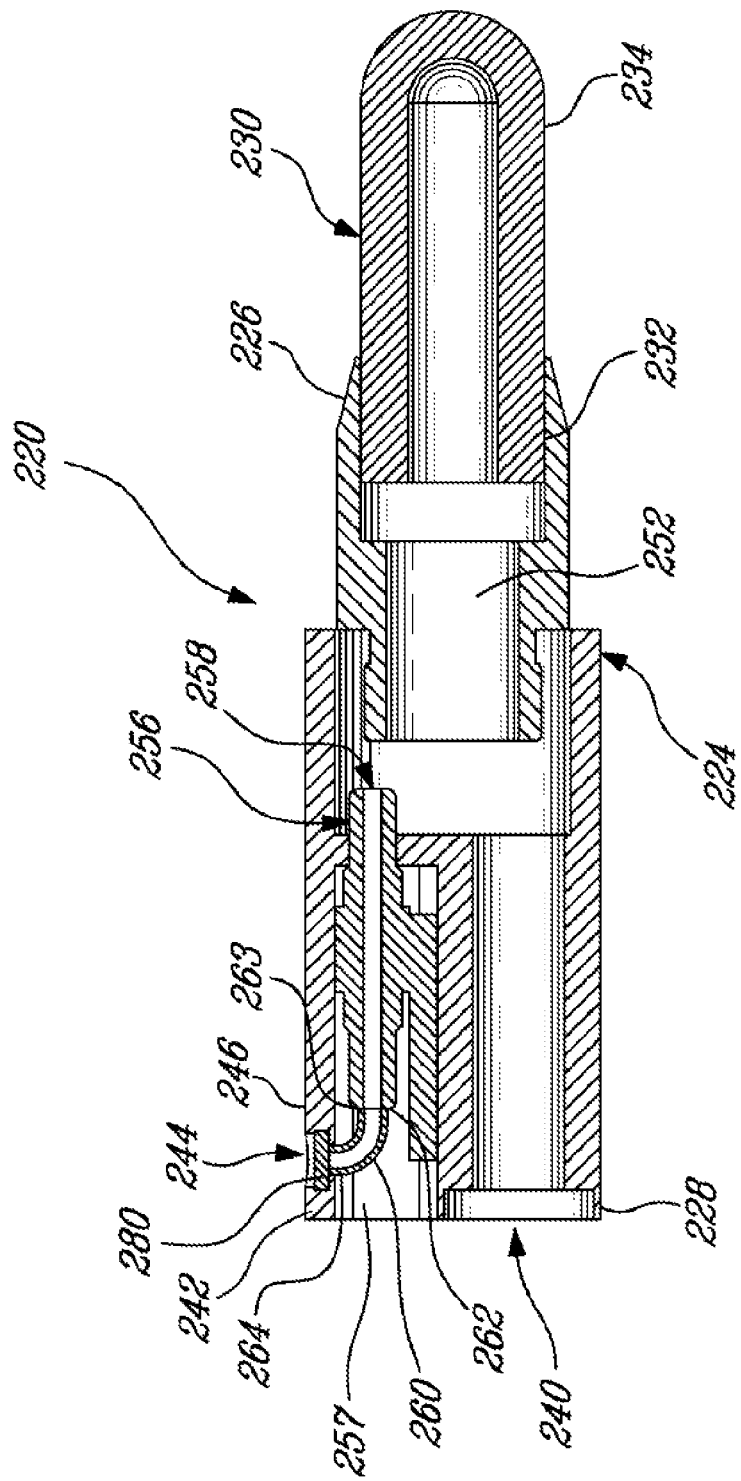
FIG. 8 is a sectional view taken along cross-section lines 8-8 of FIG. 7 of the tensiometer apparatus shown in FIG. 6.

Referring now to FIGS. 6 to 8, another embodiment of the sensing portion 220 for a tensiometer will be described wherein the features are numbered with reference numerals in the 200 series which correspond with the reference numerals of the previous embodiment. In this alternate embodiment, the housing 224 has a substantially tubular shape and the fluid chamber 252 has a substantially linear shape with a single longitudinally extending section.

As with the sensing portion 120, the sensing portion 220 has a housing 224 with a lower end 226 and an upper end 228 and a porous material tip 230, mounted to the lower end 226 of the housing 224. The porous material tip 230 has a first section 232 which extends in the housing 224 and a second section 234 which is in direct contact with the porous medium when inserted therein.

The housing 224 has a liquid inlet aperture 240 (or fluid aperture), located on an upper wall 242 of the housing 224 and a gas inlet aperture 244, located on a lateral wall 246. The liquid inlet aperture 240 is located at a first end of chamber 242, opposite to the porous material tip 230. The housing 224, including the liquid inlet aperture 240 and the gas inlet aperture 244, is entirely insertable in the porous medium for monitoring matrix water potential.

As with the previous embodiment, the fluid chamber 252 is in fluid communication with the porous material tip 230.

The pressure sensor 256 is located in the housing 224, in a pressure sensor chamber 257, external to the fluid chamber. The pressure sensor 256 has a liquid port 258 in fluid communication with the fluid chamber 252. It is also in fluid communication with the atmosphere through an atmospheric gas channel 260 which extends in the pressure sensor chamber 257. The atmospheric gas channel 260 has a first port 262 connected to a reference port 263 of the pressure sensor 256 and a second port 264 connected to the gas inlet aperture 244. The liquid pressure in the fluid chamber 252, sampled through the liquid port 258, is compared by the pressure sensor 256 to the atmospheric pressure, sampled through the gas inlet aperture 244.

As with the previously described embodiment, to prevent liquid and porous medium infiltration into the gas inlet aperture 244 and the atmospheric gas channel 260, a hydrophobic membrane 280 is inserted in the gas inlet aperture 244. The hydrophobic membrane 280 prevents partial or complete obstruction of the gas inlet aperture 244 and the atmospheric gas channel 260 which could bias the pressure measurements.

As with the previously described embodiment, an electric wire channel (not shown) can also extend longitudinally in the housing 224 and contain electric wires operatively connected to the pressure sensor 256 and to an electric circuit board (not shown).

As with the previously described embodiment, the liquid inlet aperture 240 is sealed and closed to prevent liquid contained in the fluid chamber 252 to exit therethrough and gas infiltration. The pressure sensor chamber 257 can be closed with a resin, such as epoxy, before inserting the housing 224 in the porous medium.

The sensing portions 120 and 220 operate substantially similarly to measure matrix water potential in porous media. The atmospheric pressure is obtained through the atmospheric gas channel 260 which is in gas communication with the hydrophobic membrane inserted in the gas inlet aperture 244.

In the embodiments described in reference to FIGS. 2-8, the porous material tip can have a hollow space, or a depression, therein to obtain faster kinetics, or faster time constant.

It is appreciated that even if the above described examples relate to tensiometers, the hydrophobic membrane can be mounted to various types of sensing portions such as and without being limitable to pH, salinity, temperature, humidity, liquid, gas, or gas concentration sensing portions. The sensing portion can also include a sensor detecting the irrigation status. The sensing portion can also include a LED photodetector for detecting fluid in soils or porous media.

Figure 9:
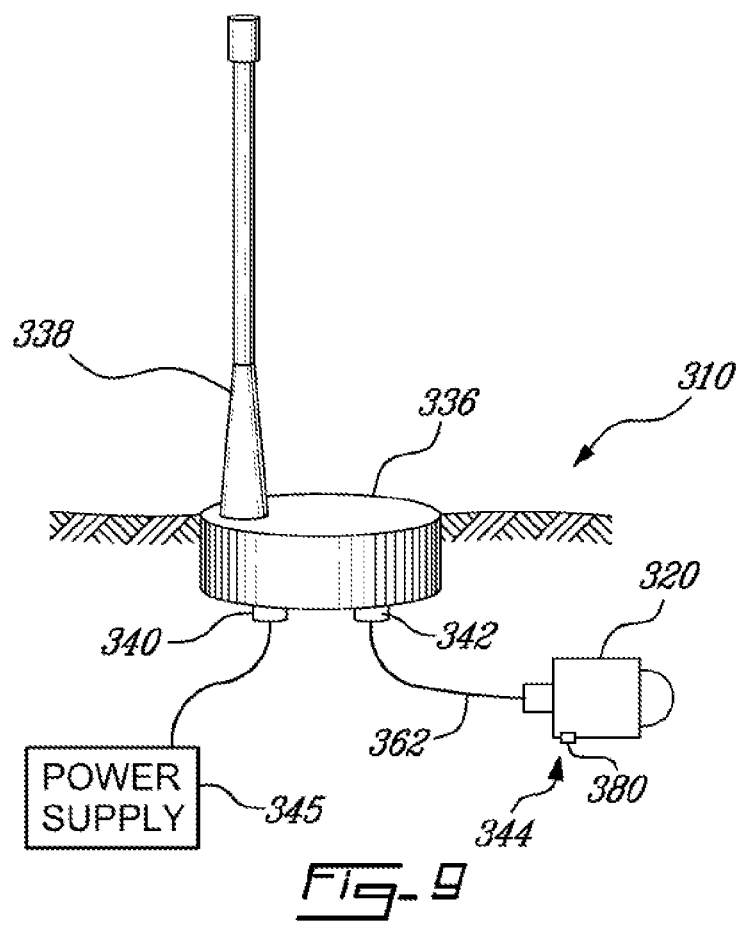
FIG. 9 is a schematic view of a modular tensiometer apparatus in accordance with an embodiment, wherein the tensiometer apparatus has an independent head.

Referring to FIG. 9, there is shown a modular porous medium sensor apparatus 310, which can be, for instance and without being limitative to a tensiometer, a pH, a salinity, a temperature, a humidity, a gas, or a gas concentration sensor, having a sensing portion 320, inserted in the porous medium, and connected to the head 336. The head 336 is separated and independent from the sensing portion 320 which can be, at least partially, inserted in the porous medium to be sampled. The head 336 and the antenna 338 extend above the porous medium when the sensing portion 320 is inserted therein.

The lower face of the head 336 can have two connectors 340, 342 extending downwardly therefrom. The connector 340 can be used to connect the sensor apparatus 310 to a power supply 345. The power supply 345 provides power to the sensor apparatus 310 and, more particularly, to the electric circuitry including an electronic circuit board, located in the head 336. The data can be transferred with wireless technology through the antenna 338 or the sensor apparatus 310 can be physically connected to a data logger through the connector 342.

The upper face of the head 336 can include an electronic dial (not shown). The electronic dial can display, amongst others, the parameter measured by the sensor 310.

The data acquired by the sensor, located in the sensing portion 320, can be transmitted through electric wires to the electronic circuit board located in the head 336. The data transferred are typically provided in millivolts and converted by the electronic circuit board. The parameter monitored by the sensor can be displayed on the electronic dial and can also be transmitted to a data logger (not shown) which records the data transmitted from the sensor.

It is appreciated that in an alternate embodiment, the information provided by the sensor and transferred to the electronic circuit board can be digital information.

It is appreciated that several sensing portions can be connected to the head 336, such as and without being limitative to a pressure, a pH, a salinity, a temperature, a humidity, a liquid, a gas, or a gas concentration sensing portion. They can be connected using flexible electrical connections 362 providing more flexibility in the positioning of the sensing portions.

In alternate embodiments, the head 336 can include any number of connectors 340, 342. Moreover, the shape of head 336 can vary. The power supply, if any, such as batteries, can be mounted in head 336.

The sensing portion 320, which can be entirely inserted in the porous medium, includes a hydrophobic membrane 380 providing gas communication between gas contained in the porous medium, substantially at atmospheric pressure, and the sensor located in the sensing portion 320. The hydrophobic membrane simultaneously prevents water and porous medium infiltration in the sensing portion 320.

Figure 10:
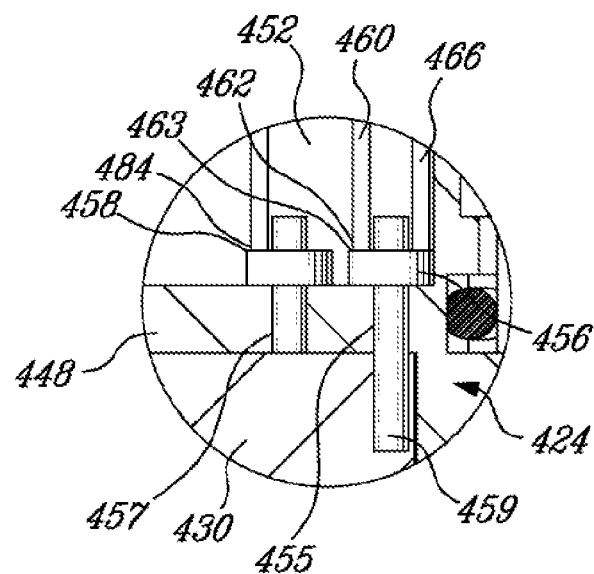
FIG. 10 is a sectional view, enlarged, of a pressure sensor in a self-priming tensiometer apparatus in accordance with an embodiment.

Referring now to FIG. 10, there is shown an internal section of a self-priming tensiometer, which can have a sensing portion similar to sensing portion 120, 220, 320. As with the previously described tensiometers, the housing 424 (only a section is shown) has an atmospheric gas aperture (not shown), similar to atmospheric gas aperture 144, 244, 344. Contrary to the previously described tensiometers, it does not include a liquid inlet aperture since it does not include a fluid chamber filled with liquid. Instead, the housing 424 has a gas outlet aperture, as it will be described in more details below.

The porous material tip 430 is mounted to the lower end of the housing 424 and has a lower section in contact with the porous medium when the housing 424 is inserted therein and an upper section covered by the housing 424. The lower end of the housing 424 is sealed to the outer surface of the porous tip 430 to prevent liquid contained in the porous medium from infiltrating the porous tip 430 therebetween. Therefore, liquid can infiltrate the porous tip 430 through the lower section and flow upwardly into the upper section but cannot infiltrate the porous tip 430 directly through the upper section.

The housing 424 has a chamber 452, isolated from the porous tip 430 with an inner wall 448, defined therein. Therefore, the chamber 452 is not in fluid communication with the porous tip 430 as in the previously described embodiments. The inner wall 448 has two apertures 455, 457 defined therein. The first aperture 455 is designed to insert therein a portion of the pressure sensor 456, i.e. an insertion member 459, while the second aperture 457 is designed to insert therein a gas exit valve 458, the purpose of which will be described in more details below.

The insertion member 459 of the pressure sensor 456 extends through the aperture 455 defined in the inner wall 448 and into the porous tip 430. Therefore, the pressure sensor 456 is in fluid communication with the porous tip 430 through the insertion member 459. The upper portion of the sensor 456 extends in the chamber 452.

The pressure of the liquid contained in the pores of the porous material tip 430 and sampled through the insertion member 459 is compared by the pressure sensor 456 to the atmospheric pressure. Therefore, the pressure sensor 456 is in fluid communication with the atmosphere through an atmospheric gas channel 460 which extends in the housing 424. The atmospheric gas channel 460 has a first port 462 connected to the reference port 463 of the pressure sensor 456 and a second port (not shown) connected to the atmospheric gas aperture. As with the previously described embodiments, the atmospheric gas aperture includes a hydrophobic membrane (not shown) preventing liquid and porous medium infiltrations while allowing gas communication therethrough. Therefore, the sensing portion can be entirely or partly inserted in the growing medium.

An electric wire channel 466 can have a first end connected to the pressure sensor 456 for data transmission.

The gas exit valve 458 is in fluid communication with the atmosphere through a gas outlet channel 484 which extends in the chamber 452. The gas outlet channel 484 provides gas communication between the gas exit valve 458 and the gas outlet aperture defined in the housing 424. The gas exit valve 458 is movable between a closed position preventing fluid communication between the porous tip material 430 and the gas outlet channel 484, and an open position allowing gas contained in the pores of the porous material tip 430 to exit therethrough and into the gas outlet channel 484.

Another hydrophobic membrane (not shown) can also be inserted in the gas outlet aperture defined in the housing 424 to prevent water and porous material infiltration therethrough which could obstruct the gas outlet channel 484. Membranes similar to the ones described above in reference to FIGS. 2-5 can be inserted in the gas outlet aperture and mounted therein with similar techniques.

To measure matrix water potential in a porous medium, the housing 424 is first at least partially inserted in the porous medium. Opposite to the tensiometers described above in reference to FIGS. 2 to 8, the self-priming tensiometer of FIG. 10 does need to be filled or refilled with water to measure matrix water potential since the porous tip 430 self-priming is induced by capillarity.

Once connected to a power supply, the sensor 456 monitors the matrix water potential in the porous medium where the tensiometer is inserted. When inserted in the porous medium, the pores of the porous material tip 430 are filled with gas. Above a threshold value (or critical suction) of matrix water potential, the pores of the porous material tip 430 fill with water, drawn from the porous medium. When the pores draw water from the porous medium, the gas exit valve 458 opens to allow gas, previously contained therein, to exit therethough and flow outwardly from the housing 424 through the hydrophobic membrane. The threshold value of matrix water potential is characteristic of the properties of the porous material and, more particularly, the pore size. Once the pores fill with water, the gas exit valve 458 closes.

When the matrix water potential in the porous medium increases, the pressure in the pores varies accordingly. Therefore, the sensor 456 compares the pressure in the pores, sampled through the insertion member 459, to the atmospheric gas pressure, provided by the atmospheric gas channel 460 and the hydrophobic membrane.

If the matrix water potential falls below the threshold value, water contained in the pores flows into the porous medium and gas, also provided by the porous medium, fills the pores. Once again, if the matrix water potential of the porous medium rises above the threshold value, the pores refill with water, drawing the latter from the porous medium and the valve 458 opens to allow gas exit.

As with the previously described embodiments, the sensing portion 120 of the self-priming tensiometer can be entirely or partly inserted in the porous medium. The hydrophobic membranes mounted to the housing can either be inserted in the porous media or can extend outwardly. In both cases, hydrophobic membranes prevent liquid and porous medium infiltration into the housing.

Moreover, the self-priming tensiometer can be a single piece, i.e. the head including the electronic components is assembled with the sensing portion, as in the embodiment shown in FIG. 1, or modular, i.e. the head including the electronic components are separated from the sensing portion and connected through electrical connections, as in the embodiment shown in FIG. 9.

Figure 11:
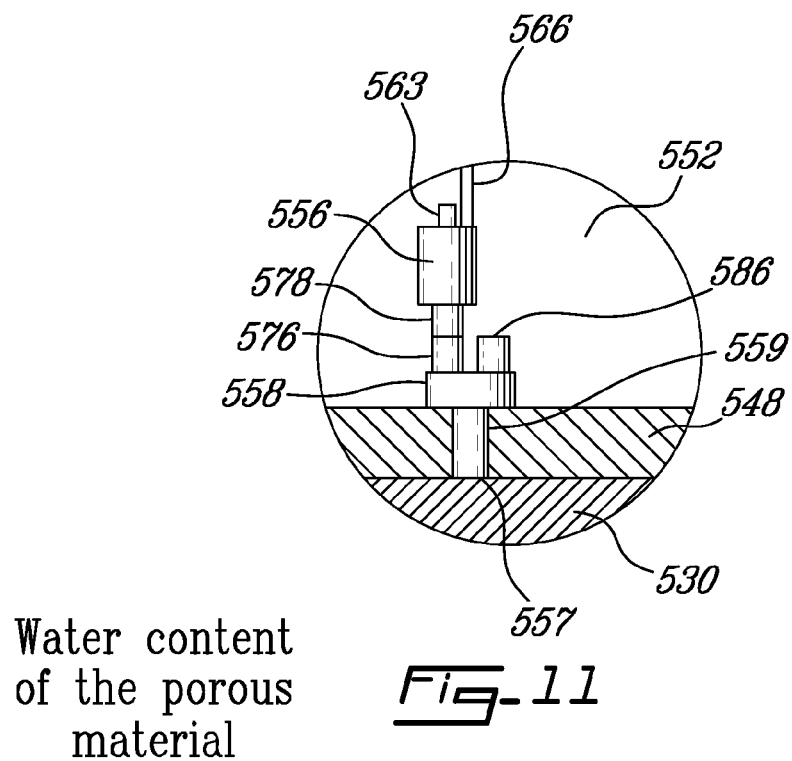
FIG. 11 is a sectional view, enlarged, of a pressure sensor in a self-priming tensiometer apparatus in accordance with another embodiment, wherein the pressure sensor is in fluid communication with a gas exit valve.

Referring now to FIG. 11, another embodiment of the self-priming tensiometer apparatus will be described wherein the features are numbered with reference numerals in the 500 series which correspond with the reference numerals of the previous embodiment. Instead of having both the gas exit valve 558 and the pressure sensor 556 in direct fluid communication with the porous tip 530, the pressure sensor 556 is in fluid communication with the porous tip 530 through the gas exit valve 558. The chamber 552 is free of atmospheric gas channel and gas outlet channel. The housing includes an atmospheric gas aperture (not shown) extending therethrough and in fluid communication with the chamber 552 and having a hydrophobic membrane mounted therein. Therefore, the gas exit valve 558 and the reference port 563 of the pressure sensor 556 are directly in fluid communication with the chamber 552.

As with the previously described embodiment, the chamber 552 is isolated from the porous tip 530 with the inner wall 548, which includes one aperture 557 therein. The aperture 557 is designed to insert therein a portion of the gas exit valve 558, i.e. an insertion member 559.

The insertion member 559 of the gas exit valve 558 extends through the aperture 557 defined in the inner wall 548 up to the porous tip 530. Therefore, the insertion member 559 provides fluid communication between the porous tip 530 and the chamber 552. The upper portion of the valve 558 extends in the chamber 552.

The liquid sampled in the pores of the porous material tip 530 flows into the valve 558 towards the sensor 556. The pressure sensor 556 and the gas exit valve 558 are in fluid communication through a liquid port 576 of the valve 558 and a liquid port 578 of the sensor 556.

As with the above described self-priming tensiometer, the pressure of the liquid contained in the pores of the porous material tip 530 and sampled through the insertion member 559 is compared by the pressure sensor 556 to the atmospheric pressure. Therefore, the pressure sensor 556 is in fluid communication with the atmosphere through the reference port 563. The reference port 563 is in fluid communication with the atmosphere through the chamber 552 and the atmospheric gas aperture, including the hydrophobic membrane, defined in the housing.

The gas exit valve 558 is in fluid communication with the atmosphere through the gas outlet port 586 which extends in the chamber 552 and is in fluid communication therewith. As mentioned above, the fluid chamber 552 is in fluid communication with the atmosphere through the atmospheric gas aperture, including the hydrophobic membrane, defined in the housing. As with the valve 458, the gas exit valve 558 is movable between a closed position preventing gas contained in the porous tip material 530 to flow into the chamber 552, and an open position allowing gas contained in the pores of the porous material tip 530 to exit therethrough and into the chamber 552.

The hydrophobic membrane, similar to the ones described above and inserted in the atmospheric gas aperture, prevents liquid and porous medium infiltration in the chamber 552.

The data monitored by the sensor 556 are transferred into an electric wire channel 566, which can extend into the chamber 552. As with the previously described embodiments, the data acquired by the pressure sensor 556 can be transmitted through electric wires to an electronic circuit board.

To measure matrix water potential in a porous medium, the self-priming tensiometer is first, entirely or partially, inserted in the porous medium, does need to be filled or refilled with water to measure matrix water potential, and its operation is similar to above described self-priming tensiometer.

It is appreciated that the hydrophobic membrane can be used in combination with other self-priming sensor apparatus for growing media/porous media such as, for instance and without being limitative to salinity sensor apparatuses.

As mentioned above, the critical suction of the porous material tip 530 depends on the characteristics of the porous material constituting the tip 530 and, more particularly, the pore size.

For the self-priming sensors, the porous material tip includes a material having a stable structure and pores of a substantially uniform size. The pore size can be designed such that the porous material tip is saturated in water over the useful range of soil matrix potential of the sensor, i.e. a range over which the porous medium is wet and water is available for plants and over which the matrix water potential of the porous medium is to be measured; but such that the porous material tip drains when the porous medium dries out from plant uptake and/or from air drying, i.e., when the content of plant available water in the porous medium is significantly low and rewetting becomes necessary. Draining of the porous material tip reinitializes the sensor and the porous material tip consequently draws a completely new solution sample each time the porous medium is rewetted and a critical suction is reached, and quickly stabilizes upon wetting of the porous medium.

In one embodiment, the porous material is a porous glass made by sintering glass powder. Pure silica or slightly altered silica powder may be used, for instance. In order to ensure a uniform pore size throughout the porous material, the glass powder is screened to obtain a glass powder of unique solid particle size. The glass powder is then sintered with controlled compaction and cooking temperature parameters such that a substantially unique and appropriate pore size and an appropriate porosity are obtained. Glass beads can be typically fritted in a furnace at temperature between 500 to 800° C. for about fifteen minutes to one hour and a half, and then cooled down. The specific size of the glass beads should be selected to obtain the pore size on the fritted matrix. A porous plastic material made by plastic powder sintering, a fiber glass material, or any other solid porous material could alternatively be used as a porous material.

Figure 12:
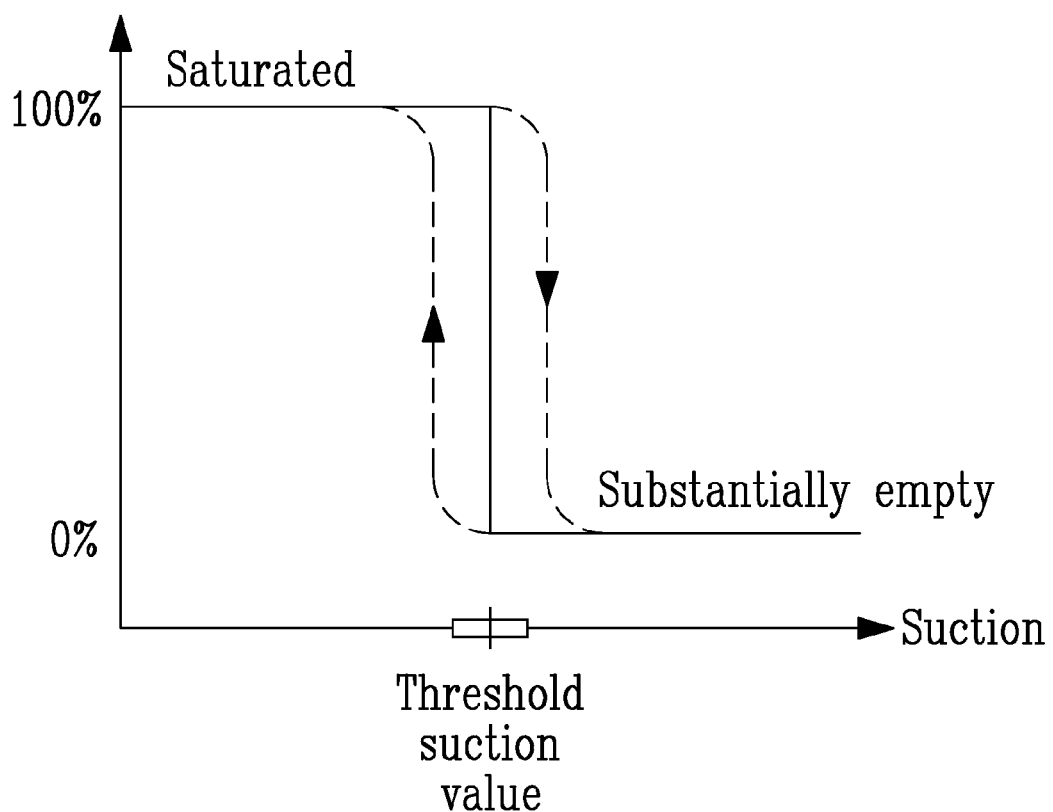
FIG. 12 is a schematic graph showing the quantity of liquid contained in a porous tip of the self-priming tensiometer apparatus as a function of the suction measured.

Now referring to FIG. 12, the water content of the porous material tip is shown as a function of the suction. The characteristics of the porous material tip, more particularly, the pore size, the pore size variance and the porosity, determine the water content response of the porous material tip. The substantially step function is mostly provided by the unique pore size. The porous material is characterized by a critical suction below which the porous material tip is substantially saturated and above which the porous material tip is substantially empty of water solution. It is noted that the suction corresponds to the absolute value of the matrix potential of the porous medium.

When the probe is inserted into a porous medium, the porous material tip equilibrates to the matrix potential of the porous medium. If the porous medium is at a suction greater than the critical suction, as a result of plant water uptake in the porous medium for example, the porous material equilibrates with the porous medium and therefore empties of water. If water is provided by irrigation or rainfall, the suction of the porous medium consequently decreases below the critical suction and the porous material tip, as a result of a new equilibrium of the porous material tip with the porous medium, draws water from the porous medium into the porous material tip. Due to a unique pore size, the porous material tip abruptly saturates when the suction drops below the critical suction.

The critical suction substantially corresponds to the limit where the porous medium contains no or very low plant available water. The porous material is substantially empty when there is no available water and is substantially saturated when there is a significant amount of available water. As described hereinabove, consequently, the water content of the porous material tip is substantially independent of the matrix potential and the water content of the porous medium when the porous medium contains plant available water (the suction is below the critical suction), and the porous material tip drains of porous medium solution as the porous medium dries out of plant available water. The porous material tip is thus initialized periodically during a normal irrigation cycle of the porous medium. As the porous medium is being watered, the critical suction is reached and the pores of the porous material tip fill and saturate with the porous medium liquid phase solution. The porous material thus draws a new solution sample each time the porous medium is being watered. The stabilization of the solution sampled by the porous material tip is thus made by convective flow, as opposed to diffusion, a process much faster than diffusion only. The porous material is consequently memory free and stabilizes in few minutes.

Ideally, the water content response curve has a step shape (solid line of FIG. 12), i.e. the pores fill or drain abruptly when the suction crosses a threshold suction value. As shown in FIG. 12 (dashed line), in reality, the pores fill and drain over a threshold suction range surrounding the threshold suction value. A hysteresis effect may also be observed. In this latter case, the threshold suction value is slightly different when the pores drain than when they fill. A small hysteresis effect should not have any substantial effect on the matrix water potential measurement but it should nonetheless be limited as possible.

The pores size is designed such that pores empty and fill over the range of matrix potential characteristic of the matrix potentials maintained in the porous medium during plant growth, according to typical irrigation set points used in fields or in greenhouses. The porous material tip automatically fills up when the soil is rewet and drains when the soil dries from plant uptake and/or from air drying. In a typical irrigation cycle of the porous medium, the matrix water potential is monitored when the porous medium is wet and over a substantially large range of the porous medium water content. As the porous medium dries out and the water matrix potential goes beyond the given critical suction determined by the characteristics of the porous material tip, the porous material tip drains and is consequently initialized. The empty range of the porous material tip corresponds to a critical water content of the porous medium where watering is nearly required because substantially no more water is available for the plants. As the porous medium is being watered, the matrix potential of the porous medium steps below the critical suction and a new solution sample is drawn by the porous material tip. The porous material tip thus periodically refills. For example, in greenhouse and nursery growing medium applications, the suitable pore size should be found between 70 to 350 µm. For use in mineral soils, the suitable pore size should be found between 2 and 20 µm. A suitable porosity of the porous material tip is typically between about 30 and 40%.

More generally, for various porous media and set points, the specific suitable pore size should be found somewhere between 1 and 1000 μm. Experimental tests have been performed using a porous material tip with a standard deviation of its pore size of about 10%. It is noted that a standard deviation below 15% should generally be suitable. Lower standard deviations are nonetheless desirable.

A wet porous medium comprises drainage water, plant available water and plant unavailable water. The critical suction is thus selected such that, over the useful range of matrix potential of the porous medium, the suction of the porous material tip matches the matrix potential of the porous medium such that the solution sampled by the porous material tip corresponds to plant available water, non-available water not being sampled.

The critical suction value depends on the characteristics of the porous material and more particularly on the size of the pores and should be adapted to the range of matrix potential of the soil in a given application of the sensor. The critical suction value should thus be adapted to the type of soil used in a particular application. Properties of the various types of soils are known in the art and are provided in Verdonck, O. F., Cappaert, T. M. and De Boodt, M. F. 1978. Physical characterization of horticultural substrates. Acta Hort. 82: 191-200. (artificial growing media) and in Koorevaar, P, G. Menelik et C. Dirksen. Elements of soil physics, Elsevier, 1983, ISBN 0-444-42242, Netherlands, p. 84-85. (mineral soils). For a given porous medium to be sampled, the specific appropriate pore size and porosity resulting in the required critical suction are typically found by experimental trials and errors.

It is appreciated that hydrophobic membranes can be inserted in gas ports of other porous medium sensors. For instance, as mentioned above, salinity sensors also include gas ports allowing gas initially contained in the pores of the porous material tip of the salinity sensors. As the pores of the porous material tip fill with water, drawn from the porous medium, gas must be released. A gas exit valve, which acts as a one-way flow control member, opens to allow gas, previously contained in the pores, to exit therethough into the internal chamber of the housing and then flow outwardly of the housing through the gas port. To prevent liquid and porous material infiltration into the internal chamber, a hydrophobic membrane is inserted therein.

Figure 13:
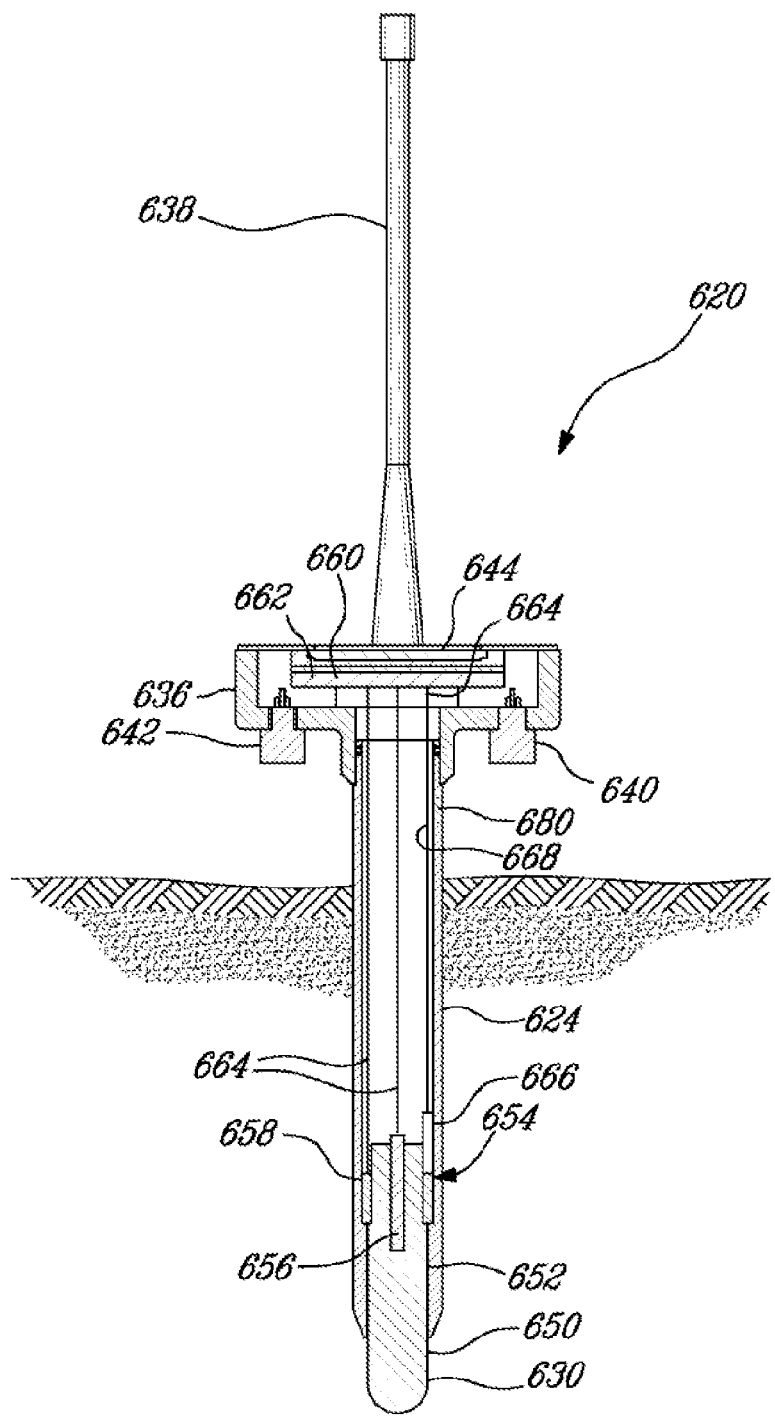
FIG. 13 is a cross-sectional view of a salinity sensor, partially inserted in a growing medium, in accordance with an embodiment.

For instance and without being limitative, FIG. 13 shows an embodiment of a salinity sensor 620 including a hydrophobic membrane 680 in accordance with an embodiment. The salinity sensor includes a porous material tip 630 having a substantially cylindrical body of porous material, with a specific pore size. The porous material tip 630 has an external section 650 extending outside the tubular housing 624 from the lower end and an enclosed section 652 located inside the tubular housing 624. When the salinity sensor 620 is at least partially inserted in the porous medium, the porous material tip 630 is in contact with the porous medium and draws water by capillarity from the porous medium through the external section 650 and to the enclosed section 652 of the porous material tip 630, and consequently samples the liquid phase solution in the porous medium. An electrical conductivity measurement, which is representative of the salinity of the solution of the porous medium, is carried out within the enclosed section 652 of the porous material tip 630 using a transducer, namely an electrical conductivity meter 654. To avoid air entrapment in the tubular housing 624, a gas exchange opening 668 is provided on the tubular housing 624 for allowing gas pressure inside the tubular housing to equilibrate with the air surrounding the sensor 620. In the embodiment shown, the air exchange opening extends above the porous medium when the sensor 620 is inserted therein while, in an alternative embodiment (not shown), the air exchange opening is located in the porous medium.

In an embodiment, the electrical conductivity meter 654 can include two electrodes 656, 658 and an electrical conductivity measuring circuit 660. The electrical conductivity measuring circuit 660 is included in an electrical circuit board 662 located in the head 636 of the salinity sensor 620. A first electrode, a straight electrode 656, is inserted in the porous material tip 630 along its middle axis. A second electrode, a ring electrode 658, surrounds the porous material tip 630, is in direct contact with its peripheral surface and is located between the porous material tip 630 and the tubular housing 624. The two electrodes 656, 658 are connected to the electrical conductivity measuring circuit 660 located in the head 636 of the salinity sensor 620, using electrical connections 664.

In order to measure the electrical conductivity of the porous material tip 630, an alternating voltage is applied to the electrodes 656, 658 and the electrical current consequently flowing in the porous material tip 630 is measured using the electrical conductivity measuring circuit 660. According to the Ohm's law, the electrical conductivity of the porous material tip 630 is found. As will be explained herein below, due to the properties of the porous material tip 630, the measured electrical conductivity is a function of the salinity of the liquid phase solution of the porous medium and is independent of the water content and the properties of the solid phase of the porous medium. The electrical conductivity measurement is thus converted into a salinity measurement according to a predetermined in-factory calibration of the salinity sensor 620.

The salinity monitored by the salinity sensor 620 can be displayed on the electronic dial 644 and can also be transmitted to a remote data logger (not shown) which records the data received from the salinity sensor 620. The data can be wirelessly transmitted through the antenna 638. Alternatively, the data can be read through the connector 642.

Another connector 640 can be used to connect the salinity sensor 620 to a power supply (not shown). The power supply may provide power to the salinity sensor 620 and, more particularly, to the electric circuitry including the electronic circuit board 662. In one embodiment, the salinity sensor 620 is self-powered using an internal power source and/or a solar battery.

A temperature measuring device 666, in this case a thermistor, can be provided in the surroundings of the porous material tip 630 and in electrical connection with the electrical circuit board 662 using the electrical connections 664. The temperature measuring device 666 is used to compensate for the predetermined variation in temperature of the relation between the electrical conductivity of the porous medium and the salinity of the sampled liquid phase solution. The temperature measuring device 666 may be an independent thermistor or thermocouple for example. Temperature compensation is achieved using this independent temperature reading. The independent temperature reading is provided to the electrical circuit board 662 which directly performs a temperature compensation of the salinity measurement.

The electrical conductivity of the liquid phase of the porous medium is measured in the porous material tip 630. The liquid phase fills the pores and the apparent electrical conductivity of the filled porous material tip 630 is measured and converted into a salinity measurement. The electrical conductivity of a porous material containing a liquid, such as the porous material tip 630, is given by the following equation:

$$\sigma_b = \theta \tau \sigma_l + \sigma_s$$

where $\sigma_b$ is the apparent electrical conductivity of the porous material, $\sigma_l$ is the electrical conductivity of the liquid phase, $\sigma_s$ is the electrical conductivity of the solid phase, $\theta$ is the fluid content of the porous material and $\tau$ is the electrical tortuosity factor, i.e., the ratio of the real to the apparent length for electron movement in a porous material. As mentioned above for the self-priming sensors, the porous material tip 630 is characterized by a unique water content upon wetting, i.e., $\theta$ is constant. Furthermore, it is made of a material having a stable structure, therefore providing a constant electrical tortuosity factor $\tau$, and having no electrical conductivity when the pores are empty of water solution or filled with pure water, i.e., $\sigma_s$ is null. Because of these characteristics, the apparent electrical conductivity $\sigma_b$ in the porous material tip 630 is independent of the structure, the water content and the electrical conductivity of the solid phase of the sampled porous medium. As long as the sensor is operated over a predetermined useful range of matrix potential of the sampled porous medium, such that the pores of the porous material tip 630 are saturated, the electrical conductivity of the porous material tip 630 is a unique function of the salinity of the liquid phase of the sampled porous medium. This implies that, over the predetermined range of matrix potential of the porous medium, there exists a single relationship between the electrical conductivity of porous material tip 630 and the salinity of the sampled liquid phase of the porous medium. Furthermore, the porous material tip 630 has no memory as it is drained and refilled, because ions in the liquid phase of the porous medium are not sorbed on the pore surface of the porous material (no permanent or variable electrical charges).

It is noted that the salinity sensor may have different shapes. For example, a rectangular block of porous material or a plate of porous material may be used as a tip. For example, two plate electrodes located on opposite sides of the porous material may then be used for measuring the electrical conductivity. An electrically isolating casing could then be used for preventing an electrical current between the two electrodes to circulate outside the porous material.

It is also noted that the parameter of the liquid phase solution measured by the sensor may vary. For example, the electrical conductivity only, rather than the salinity, of the liquid phase solution may be measured and outputted by the sensor. Furthermore, the electrical conductivity meter described herein measures the electrical conductivity in the porous material tip but it is noted that it may be replaced by another electrical transducer measuring a different electrical quantity in other applications. For example, an electrical current or an electrical potential can be measured. For example, a chemically selective transducer comprising selective electrodes may be used, the electrical transducer measuring an electrical potential at the electrodes. A sensor for measuring the pH of the liquid phase solution can be constructed using an $H^+$-selective transducer, for example, which measures the concentration of $H^+$ in the liquid phase solution. The concentration in other ions or in other components in solution in the liquid phase solution can also be measured. For example, nitrate sensors for measuring the concentration of nitrate in the solution can be constructed using nitrate-selective electrodes.

It is appreciated that there are other possible embodiments of the salinity sensor. For instance and without being limitative, a four-electrode Wenner arrangement (with ring or straight electrodes) can be used instead of the two-electrode arrangement of FIG. 13.

Figure 14:
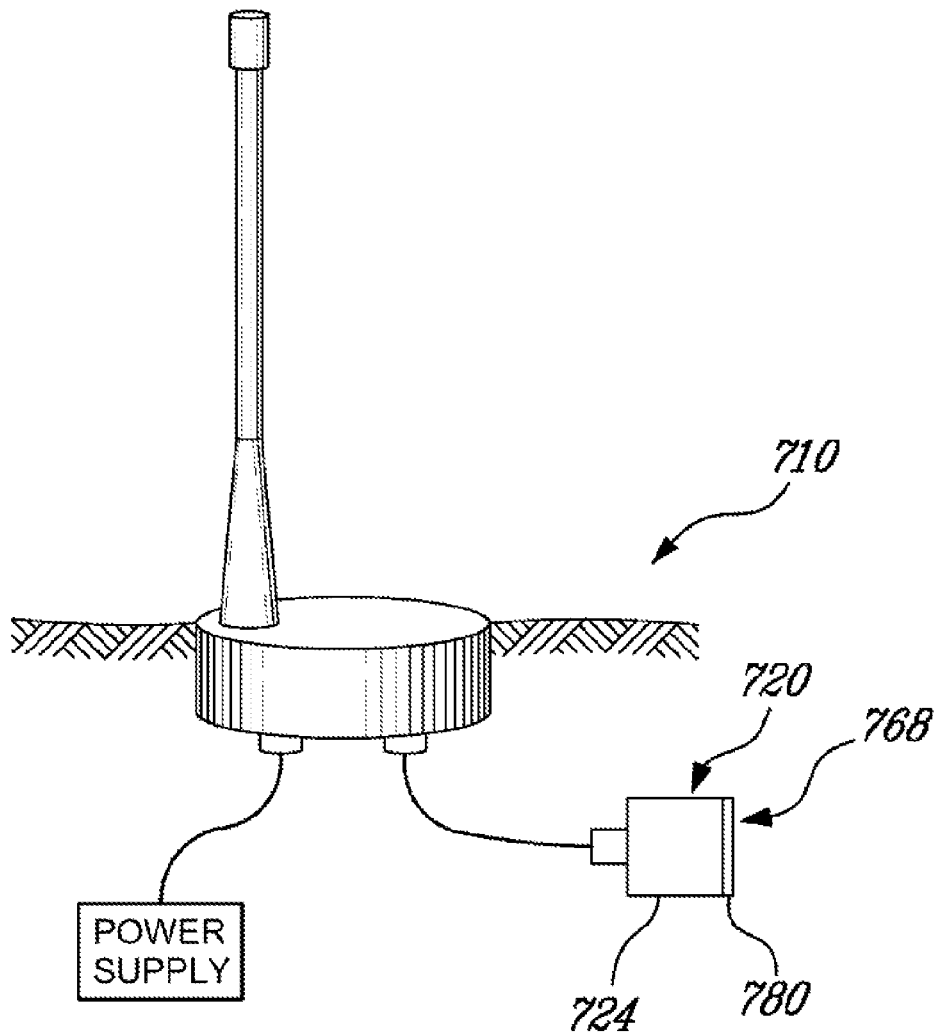
FIG. 14 is schematic view of a modular gas concentration sensor in accordance with an embodiment.

FIG. 14 shows an embodiment of a modular gas concentration sensor 710 including a sensing portion 720, inserted in the porous medium, and substantially similar to the modular tensiometer 310 shown in FIG. 9. The sensing portion 720 includes a housing 724 defining an internal chamber (not shown) and having a gas exchange opening 768 in gas communication with the internal chamber. A hydrophobic membrane 780, which can be similar to the ones described above, is mounted to the housing 724 and into the gas exchange opening 768, preventing liquid from entering into the chamber. A first surface of the hydrophobic membrane 780 is in direct contact with the porous medium when the sensing portion 720 is inserted therein while the opposite surface is in gas communication with the internal chamber of the housing 724. The housing 724 can further include a sensor for measuring, for instance and without being limitativel to the gas concentration or the concentration of a particular gas constituent in the porous medium where the sensing portion 720 is inserted using electric circuitry or spectrophotometric approaches.

The hydrophobic membrane is used to prevent water and porous medium infiltration in the housing, or between two chambers of the housing. It can be used with modular or single piece sensor apparatuses, with apparatuses where the gas port extend inwardly or outwardly of the porous medium, or with self-priming or filled fluid chamber sensor apparatuses, and any combination thereof.

It is appreciated that the hydrophobic membrane can be replaced by any liquid repellent membrane which is designed to prevent liquid and porous medium infiltration in the housing, or from one chamber to another chamber of the housing.

Referring now to FIGS. 15 and 16, it will be seen another embodiment of a porous medium sensor and, more particularly, a tensiometer apparatus 820 (or water potential sensor) wherein the tensiometer apparatus 820 has a cover 870 mounted to the upper end 828 of the housing 824 and covering the gas inlet aperture 844 extending through the lateral wall 846 of the housing 824. As mentioned above, the gas inlet aperture 844 is entirely insertable in the porous medium for monitoring matrix water potential. A hydrophobic membrane 880 is inserted in the gas inlet aperture 844 to prevent liquid and porous medium infiltration in the tensiometer apparatus 820.

The internal structure of the tensiometer apparatus 820 will not be described in further details since it can be similar to any of the above described structures.

The cover 870 is mounted to the upper end 828 of the housing 824. It has a peripheral wall 872 and an internal partition wall 874 separating the cover 870 into an upper section 876 and a lower section 878. The combination of the peripheral wall 872 and the internal partition wall 874 defines a lower internal spacing 881 in which the upper end 828 of the housing 824 is removably insertable and an upper internal spacing 882. When mounted to the upper end 828 of the housing 824, the lower section 878 of the peripheral wall 872 covers the gas inlet aperture 844. A recess 884 is defined internally in the lower section 878 of the peripheral wall 872 to ensure gas supply to the gas inlet aperture 844. The recess 884 is in registry with the gas inlet aperture 844 when the cover 870 is mounted to the housing 824. In the embodiment shown, the recess 884 extends circumferentially in the lower section 878.

For securing the cover 870 to the housing 824, the inner faces of the peripheral wall 872 and the lateral wall 846 of the housing 824 have complementary threads (not shown) so that the cover 870 can be screwed to the housing 824. Thus, the cover 870 is removably securable to the housing 824. The tightness of the cover 870 mounted to the housing 824 is such that gas can flow between the lower internal spacing 881 and the atmosphere or the porous medium in which the tensiometer 820 is inserted but infiltration of granular material from the porous medium therebetween is substantially prevented. There is thus a narrow spacing between the lower section 878 of the peripheral wall 872 and the lateral wall 846 of the housing 824 in which gases can flow but infiltration of granular material is substantially prevented.

To promote gas exchange between the atmosphere or the porous medium and the gas inlet aperture 844, the partition wall 874 has an aperture 888 defined therein. Thus, gas can flow through the upper internal spacing 882, into the partition wall aperture 888, in the narrow spacing between the cover 870 and the lateral wall 846 of the housing 824, and, finally through the gas inlet aperture 844. Gas can also flow directly from a lower edge of cover 870 and into the lower internal spacing 881.

It is appreciated that the gas inlet aperture 844 can have an hydrophobic membrane 880 inserted therein. In an alternative embodiment, the gas inlet aperture 844 can be membrane free. If the gas inlet aperture 844 is membrane free, solely the cover 870 prevents obstruction thereof.

Furthermore, it is appreciated that the tensiometer 820 can have more than one aperture covered by the cover 870.

The upper section 876 of the peripheral wall 872 has an aperture 890 defined therein for securing a cord, a cable, or a chain therein (not shown). Thus, when the tensiometer 820 is inserted in the porous medium, a section of the cord, the cable, or the chain remains exposed outwardly of the porous medium and can be pulled to withdraw the tensiometer 820 from the porous medium. It is appreciated that the cord, a cable, or a chain can be secured to the cover 870 or the housing 824 by any other appropriate means. Furthermore, other optional components can be used for identifying and pulling the buried tensiometer 820.

In an alternative embodiment, the cover 870 and/or the tensiometer 820 can include a tube (not shown) having a first end connected to the gas inlet aperture 844 and in gas communication therewith and a second end extending above the porous medium. The tube can allow gas communication between atmosphere and the gas inlet aperture 844. In another embodiment, the tube extends above the tensiometer housing 824 but its second end remains in the porous medium, close to the porous medium surface to avoid a wet soil zone and/or compacted soil layers. If the second end is located in the porous medium, the tube can include a cap preventing water and porous medium infiltration in the tube but including perforations and/or channels with baffles extending therein allowing air circulation. It could also include the hydrophobic membrane 880. In this embodiment, the tube is part of the housing and defines the gas inlet aperture 844. In an alternative embodiment, the tensiometer 820 can include two hydrophobic membranes: a first one mounted in the gas inlet aperture 844 and a second mounted in the tube, close to a second end thereof.

If the sensing portion 820 is only partially inserted in the porous medium, the gas inlet aperture 844 can extend outwardly of the porous medium. In this alternative embodiment, the cover 870 only prevents accidental porous medium infiltration in the gas aperture 844.

Therefore, the cover 870 can be mounted to conventional tensiometers which are not entirely inserted in the porous medium. It is appreciated that the cover 870 can be used with tensiometers having the pressure sensor located externally of the fluid chamber or in the fluid chamber. It is appreciated that the cover 870 can be associated with several types of tensiometers.

It is appreciated that the cover can be mounted to other porous medium sensor apparatus such as and without being limitative to a pH, a salinity, a temperature, a humidity, a gas, or a gas concentration sensor. The gas inlet aperture 844 can be entirely inserted in the porous medium thus gas communication occurs through the porous medium or it can extend outwardly of the porous medium.

The embodiments of the invention described above are intended to be exemplary only.

It will be appreciated that a plurality of sensing apparatuses can be distributed all over the field, the greenhouse or the nursery and are connected to a central station (not shown). For example, the sensing apparatuses can be connected to the central station using radio frequency but they could also be connected by wire or using any other wireless technology such as cell phone technology, satellite telecommunications or an Internet connection using, for example, a cell phone or a device such as a BlackBerry® to connect to the Internet. Each sensing apparatuses can be adapted to repeatedly transmit the sensed data and to also transmit self-check data, such as the battery charge level. The self-check data can be simply Boolean data stating a low battery charge or a low water level. The water level, if any, can be not directly monitored but can be inferred from the sensed data received at the central station. Alternatively, the water level could be directly read by a sensor and transmitted to the central station. The remote check of the sensing apparatuses is thus provided either using a self-check data transmission, by signal processing of the sensed data at the central station or using a combination of the latter two. Thanks to this feature, the grower is not required to routinely do a round check of the sensing apparatuses in the field but can rely on data received at the central station to plan the maintenance of the sensing apparatuses. He will thus only have to go in the field to look for the sensing apparatuses when maintenance is actually required and he will only have to look for the specific sensing apparatuses that require maintenance.

In order to assist the grower in locating the sensing apparatuses in the field or in the greenhouse, each sensing apparatus can additionally include a global positioning system (GPS), or any other appropriate positioning system, that provides the position of the sensing apparatuses in real time. The sensing apparatus coordinates are transmitted to central station where the grower can read the exact position of each sensing apparatus in the field. In one aspect, it allows him to easily locate the sensing apparatuses to be maintained. In a second aspect, the exact position of each sensing apparatus is used by the field monitoring software to provide a very accurate map of the soil condition which is very useful in water management and hydrozoning, i.e. providing specific irrigation for each group of plant. Installation of the sensing apparatus system in the field is also facilitated as the installer does not need to note the position of each sensing apparatus as it is installed in the field in order to allocate a field zone to each sensing apparatus.

In alternative embodiments, it will be appreciated that the peripheral wall can either be made of a transparent or opaque material. Opaque tubes provide the advantage of having no algae growth within the sensing apparatuses.

The sensor, or a portion of the sensor, reference ports, sections of the atmospheric gas channels and the electric wire channel, the valve, and/or the gas outlet channel can be embedded (or encapsulated) in a substantially solidified material, such as resin or rigid tubing, to stabilize and protect these components within the sensing apparatuses.

It will be appreciated that the shape of the sensing apparatuses can vary, that the power supply can be integrated within the sensing apparatuses. The position of the apertures in the housing can be located elsewhere. The electric wires can extend directly from the pressure sensor to the electronic circuit board, i.e. not in the wire channel.

It will also be appreciated that the electronic circuit board can be located elsewhere in the housing. For tensiometers, several types of pressure sensors, which can or cannot compensate for temperature variations, can be used. For example, a piezoresistive pressure transducer can be used.

The electronic circuit board can be replaced by any electronic or mechanical device which can process pressure data.

The sensing apparatuses described above can be calibrated at the factory, i.e. the readings, in milivolts, obtained from the sensor are automatically converted into conventional parameter readings by electronics, which prevents the need to run conversion.

The liquid filing system of the tensiometers described in reference with FIGS. 2-8, can differ.

As mentioned above, it is appreciated that a similar hydrophobic membrane can be used with other porous medium sensor apparatuses. The parameter measured in the liquid phase solution varies accordingly. For instance, it can be used with porous medium sensors having pH, salinity, temperature, humidity, gas, or gas concentration sensing portions, wherein gas communication between two sections or between a section and atmosphere is wanted while, simultaneously, preventing liquid and porous medium infiltration.

The scope of the invention is therefore intended to be limited solely by the scope of the appended claims.

What is claimed is:

1. A porous medium sensor apparatus comprising: a sensing portion at least partially insertable into a porous medium, the sensing portion having a housing with an outer wall and a gas exchange aperture extending through the outer wall in a section in contact with the porous medium when the sensing portion is at least partially inserted therein and a water-repellent membrane mounted to the gas exchange aperture, the water-repellent membrane preventing water communication through the gas exchange aperture; and a parameter sensor mounted in the housing for measuring a parameter of the porous medium in which the sensing portion is inserted.

2. The porous medium sensor apparatus as claimed in claim 1, wherein the sensing portion comprises an internal chamber in gas communication with the porous medium in which the sensing portion is at least partially inserted through the water repellent membrane.

3. The porous medium sensor apparatus as claimed in claim 1, wherein the water repellent membrane is in direct gas communication with a port of the parameter sensor and is porous and gas permeable.

4. The porous medium sensor apparatus as claimed in claim 1, wherein the water repellent membrane has a first face contacting the porous medium when the sensing portion is at least partially inserted therein and a second face, opposed to the first face and extending in the housing, gas pressures on the first and the second faces of the water repellent membrane being substantially equal.

5. The porous medium sensor apparatus as claimed in claim 1, wherein the water repellent membrane comprises a material selected from a group consisting of: porous hydrophobic polypropylene and porous hydrophobic polyethylene.

6. The porous medium sensor apparatus as claimed in claim 1, wherein the sensing portion comprises a matrix water potential sensing portion and the parameter sensor comprises a pressure sensor having a first port in fluid communication with the porous medium and providing an indication of liquid pressure in the porous medium and a second port in gas communication with the water membrane and providing an indication of atmospheric gas pressure.

7. The porous medium sensor apparatus as claimed in claim 6, wherein the second port and the water repellent membrane are in gas communication through a gas channel extending in the housing.

8. The porous medium sensor apparatus as claimed in claim 1, wherein the parameter sensor is selected from a group consisting of: an electrical transducer, a pressure sensor, a H+-selective transducer, an ion-selective transducer, a temperature sensor, a humidity sensor, a liquid sensor, and a gas sensor.

9. The porous medium sensor apparatus as claimed in claim 1, wherein the water-repellent membrane prevents water infiltration in the housing through the gas exchange aperture and allows gas communication between atmosphere and the housing through the porous medium; the porous medium sensor apparatus further comprising:
a porous tip mounted to the housing, insertable into the porous medium simultaneously with the housing, having pores fillable with liquid solution, and the pores being in gas communication with the housing through a one-way flow control member, gas communication between the porous tip and atmosphere being allowed via the one-way flow control member and the water-repellent membrane; and wherein
the parameter sensor measures a quantity in said liquid solution, the pores of the porous tip being in fluid communication with the sensor, said quantity being representative of said parameter in said porous medium.

10. The porous medium sensor apparatus as claimed in claim 9, wherein the housing comprises an internal chamber, the water-repellent membrane preventing water infiltration in the internal chamber through the gas exchange aperture and allowing gas communication between atmosphere and the internal chamber, the pores of the porous tip being in gas communication with the internal chamber through the one-way flow control member.

11. The porous medium sensor apparatus as claimed in claim 9, wherein the housing comprises a gas exchange channel having a first port connected to the one-way flow control member and a second port connected to the water-repellent membrane, the water-repellent membrane preventing water infiltration in the gas exchange channel through the gas exchange aperture and allowing gas communication between the porous medium and the gas exchange channel, the pores of the porous tip being in gas communication with the gas exchange channel through the one-way flow control member.

12. The porous medium sensor apparatus as claimed in claim 1, wherein:
the water-repellent membrane covers the gas exchange aperture, prevents water infiltration in the housing therethrough, and allows gas communication with atmosphere through the porous medium; and
the parameter sensor has a reference port in gas communication with the water-repellent membrane.

13. The porous medium sensor apparatus as claimed in claim 12, wherein the water-repellent membrane is porous and gas permeable and inserted into the porous medium when the housing is inserted therein.

14. The porous medium sensor apparatus as claimed in claims 12, wherein the parameter sensor comprises a pressure sensor having a first port in fluid communication with the porous medium and providing an indication of liquid pressure in the porous medium and a second port in gas communication with the water-repellent membrane and providing an indication of atmospheric gas pressure, the second port and the water-repellent membrane being in fluid communication through a liquid free chamber defined in the housing.

15. The porous medium sensor apparatus as claimed in claim 1 wherein the parameter sensor comprises:
a pressure sensor mounted in the housing and having a reference port in gas communication with atmosphere through the water repellent membrane, a liquid port in fluid communication with the porous medium when the housing is inserted therein, the pressure sensor providing an indication of a matrix water potential by comparing liquid pressure in the liquid port and gas pressure in the reference port.

16. The porous medium sensor apparatus as claimed in claim 15, wherein the sensing portion comprises an internal chamber in gas communication with the porous medium in which the sensing portion is at least partially inserted through the water repellent membrane and in liquid communication with the porous medium in which the sensing portion is at least partially inserted through a porous tip, the water-repellent membrane extending over the gas aperture and preventing water infiltration in the housing.

17. The porous medium sensor apparatus as claimed in claim 1, wherein
the water-repellent membrane is in direct contact with the porous medium and allows gas communication with atmosphere through the porous medium;
the parameter sensor comprises a pressure sensor mounted in the housing and having a reference port in gas communication with the water-repellent membrane; and
the porous medium sensor apparatus further comprises a porous tip mounted to the housing, insertable into the porous medium simultaneously with the housing, having pores fillable with liquid, and the pores being in fluid communication with the pressure sensor, the pressure sensor providing an indication of the matrix water potential by comparing the pressures in atmosphere through the reference port and in the porous tip.

18. The porous medium sensor apparatus as claimed in claim 1, wherein the water-repellent membrane is recessed in the gas exchange aperture and spaced-apart from a lateral wall of the housing.

19. The porous medium sensor apparatus as claimed in claim 1, wherein the water-repellent membrane is in direct contact with the porous medium when the sensing portion is at least partially inserted therein.

20. A porous medium sensor apparatus comprising: a sensing portion at least partially insertable into a porous medium, the sensing portion having a housing with a gas exchange aperture defined therein and a water-repellent membrane mounted to the gas exchange aperture, the water-repellent membrane preventing water communication through the gas exchange; and a cover mounted to the housing and covering the gas exchange aperture, the cover substantially preventing granular material to obstruct the gas exchange aperture while allowing gas communication between atmosphere and the gas exchange aperture; and a parameter sensor mounted in the housing for measuring a parameter of the porous medium in which the sensing portion is inserted.

21. The porous medium sensor apparatus as claimed in claim 20, wherein the cover comprises a peripheral wall abutting the housing with a tightness substantially preventing granular material to infiltrate in between while allowing gas communication and having a recess defined internally therein in register with the gas exchange aperture.

* * * * *